(12) United States Patent
Glusker et al.

(10) Patent No.: US 10,967,139 B2
(45) Date of Patent: Apr. 6, 2021

(54) MULTIDOSE INHALER

(71) Applicant: Novartis AG, Basel (CH)

(72) Inventors: Mark Glusker, East Hanover, NJ (US); Alex Yulan Chiao, East Hanover, NJ (US); George Axford, East Hanover, NJ (US); Colleen Patricia Serafin, East Hanover, NJ (US); Jonathan Patrick Summers, San Francisco, CA (US); Jonathan Paul Downing, San Francisco, CA (US)

(73) Assignee: Novartis AG, Basel (CH)

( * ) Notice: Subject to any disclaimer, the term of this patent is extended or adjusted under 35 U.S.C. 154(b) by 169 days.

(21) Appl. No.: 16/070,930

(22) PCT Filed: Jan. 17, 2017

(86) PCT No.: PCT/IB2017/050246
§ 371 (c)(1),
(2) Date: Jul. 18, 2018

(87) PCT Pub. No.: WO2017/125853
PCT Pub. Date: Jul. 27, 2017

(65) Prior Publication Data
US 2019/0015608 A1   Jan. 17, 2019

Related U.S. Application Data

(60) Provisional application No. 62/322,962, filed on Apr. 15, 2016, provisional application No. 62/280,264, filed on Jan. 19, 2016.

(51) Int. Cl.
*A61M 15/00* (2006.01)
*A61M 16/14* (2006.01)

(52) U.S. Cl.
CPC .... *A61M 15/0051* (2014.02); *A61M 15/0025* (2014.02); *A61M 15/0028* (2013.01);
(Continued)

(58) Field of Classification Search
CPC .............. A61M 15/00; A61M 15/0001; A61M 15/0021; A61M 15/0025; A61M 15/0028;
(Continued)

(56) References Cited

U.S. PATENT DOCUMENTS 5,740,794 A * 4/1998 Smith ............... A61M 15/0045
128/203.15
2003/0172927 A1* 9/2003 Young ............... A61M 15/0031
128/203.15
(Continued)

FOREIGN PATENT DOCUMENTS

CN      10450721 A      4/2015
CO      01009472        8/2001
(Continued)

*Primary Examiner* — Joseph D. Boecker
(74) *Attorney, Agent, or Firm* — Guy Tucker; Michael Mazza

(57) ABSTRACT

The present invention relates to an inhaler which comprises a durable unit and a replaceable (cartridge) unit, and which comprises systems, subsystems and elements to provide an "open-inhale-close" user experience. A durable unit comprises a breath-actuated trigger mechanism, and optionally electronics for providing user feedback, and telehealth can capability. A replaceable unit comprises a mouthpiece, blister strip, aerosol path dose counter and a blister piercing and aerosolization engine assembly assembly. A lockout mechanism may be provided to prevent further use of the cartridge when the dose counter reaches a preselected limit, such as zero.

14 Claims, 15 Drawing Sheets

(52) U.S. Cl.
CPC .... *A61M 15/0035* (2014.02); *A61M 15/0041* (2014.02); *A61M 15/0045* (2013.01); *A61M 15/0091* (2013.01); *A61M 16/14* (2013.01); *A61M 15/007* (2014.02); *A61M 2202/064* (2013.01); *A61M 2205/123* (2013.01)

(58) Field of Classification Search
CPC .......... A61M 15/0035; A61M 15/0036; A61M 15/0038; A61M 15/0041; A61M 15/0045; A61M 15/0048; A61M 15/0051; A61M 15/0063; A61M 15/0065; A61M 15/0068; A61M 15/007; A61M 15/0081; A61M 15/0091
See application file for complete search history.

(56) References Cited

U.S. PATENT DOCUMENTS

| | | | |
|---|---|---|---|
| 2005/0154491 A1* | 7/2005 | Anderson | A61M 15/008 700/236 |
| 2007/0062525 A1 | 3/2007 | Bonney et al. | |
| 2007/0119450 A1 | 5/2007 | Wharton et al. | |
| 2007/0137645 A1* | 6/2007 | Eason | A61M 15/0025 128/203.15 |
| 2007/0235029 A1 | 10/2007 | Zhu et al. | |
| 2008/0177246 A1 | 7/2008 | Sullivan et al. | |
| 2008/0196718 A1* | 8/2008 | Connell | A61M 15/0025 128/203.15 |
| 2009/0283095 A1 | 11/2009 | Pocock | |
| 2010/0059052 A1* | 3/2010 | Davies | A61M 15/0055 128/203.15 |
| 2010/0258118 A1* | 10/2010 | Morton | A61M 15/0036 128/203.15 |
| 2015/0151059 A1 | 6/2015 | Meliniotis | |

FOREIGN PATENT DOCUMENTS

| | | |
|---|---|---|
| DE | 202005004661 | 8/2005 |
| EP | 0 467 172 | 1/1992 |
| EP | 2 082 759 | 7/2009 |
| GB | 2407042 | 4/2005 |
| GB | 2407042 A | 4/2005 |
| RU | 2369411 C2 | 10/2019 |
| WO | WO 2011/083377 | 7/2011 |
| WO | WO 2013/175176 | 11/2013 |

* cited by examiner

30

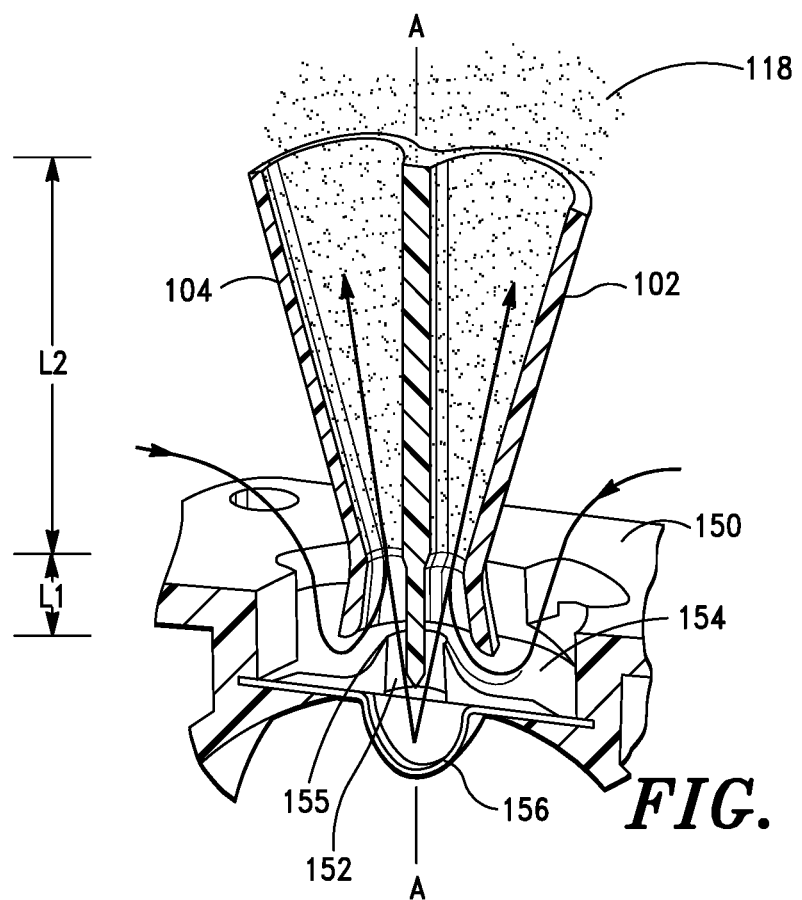
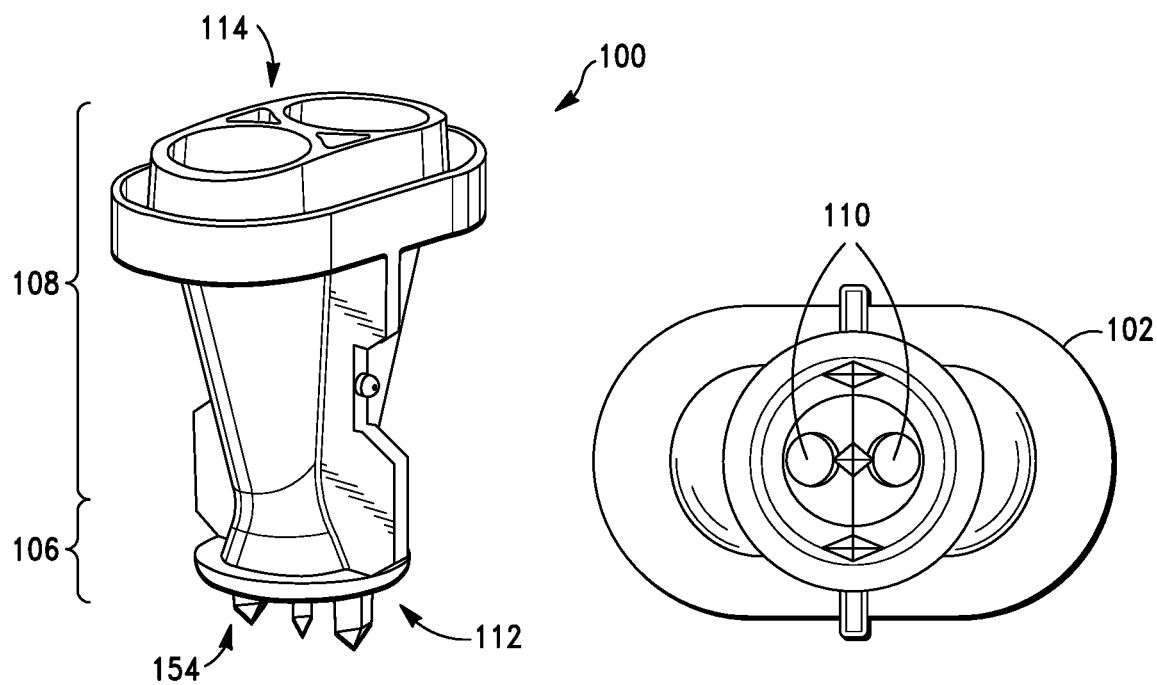
FIG. 5a
FIG. 5b FIG. 5c

MULTIDOSE INHALER

BACKGROUND OF THE INVENTION

Field of the Invention

The present invention relates to an inhaler device for pulmonary delivery of medicaments, and particularly to a multidose inhaler device that utilizes a blister strip comprising a plurality of blisters containing a powdered medicament. In one aspect, the invention relates to a device and methods for dispersing dry powder medicaments for inhalation by a patient.

Background of the Invention

Inhaleable drug delivery, where an aerosolized medicament is orally or nasally inhaled by a patient to deliver active pharmaceutical ingredients to the patient's respiratory tract, has proven to be a particularly effective method and/or desirable alternative to other forms of drug delivery. Many types of inhalation devices are configured to allow a user to inhale medicament to receive an active pharmaceutical ingredient contained therein, including devices that aerosolize a dry powder medicament. Some inhalers contain multiple doses of medicament which can be sequentially accessed by a user, while others are capsule/blister based and require a user to insert at least one capsule/blister into the device for each delivery.

It is often desirable or convenient to deliver a medicament to a patient pulmonarily, using a dispensing device, such as an inhaler device (or simply, an "inhaler"). The inhaler device may be adapted to dispense a product, for example a medicament dose, from blisters within which a discrete dose of a medicament is stored. In such inhalers, the medicament is typically in a powdered form to be inhaled by a patient. Conventionally, blister-based unit dose inhalers use blister packs having only a single blister cavity which may be inserted, opened, and the medicament inhaled therefrom. However, such single dose inhalers may not be convenient for all patients since additional individual blisters must be carried independently of the inhaler device in order for a patient to take multiple doses over a period of time. Additionally, unit dose inhalers require the patient to locate, manipulate, insert and remove the blister each time a medicament dose is desired.

Accordingly, multiple dose inhalers that use a blister strip have been developed. In such inhalers, the blister strip has a plurality of blisters thereon and the strip is moved (longitudinally or rotationally) so that blisters are sequentially presented to a dispensing position from which the medicament may be dispensed to the patient, such as during inhalation. The blisters are opened when they are positioned in the dispensing position, or as they are moved to the dispensing position.

Dry-powder inhalers (DPI) are one of popular inhaleable drug delivery devices, intended to enable the delivery of medicament from the capsule/blister to an airway, for example the lung, of a patient. The medicament may be a dry powder formulation and may include one or more active compounds for treating one or more disease states. The medicament such as dry powder drug formulations can comprise one or more active agents including an agent, drug, biologic, compound, composition of matter or mixture thereof which provides some pharmacologic, often beneficial, effect. The medicament also can optionally be mixed with one or more pharmaceutical excipients which are suitable for pulmonary administration. Moreover, the medicament may be substantially devoid of an active component, for example the medicament may be a placebo.

SUMMARY OF THE PRESENT INVENTION

The present invention comprises an inhaler which comprises a durable unit or body and a replaceable (cartridge) unit. The invention is further directed to elements, aspects or sub-assemblies of the device; such as mechanisms, aerosolization engine, receptacle piercing and/or powder fluidization mechanism, breath actuated trigger mechanism, dose counting and lock-out mechanism or systems, telehealth and/or monitoring capabilities, and device modularity. In aspects of the invention, the primary subsystems are considered to be priming, latching/unlatching, receptacle piercing, receptacle indexing, and end-of-life lockout. In aspects of the invention, mechanisms which comprise priming, latching/unlatching and receptacle piercing are considered to define an automatic blister opening mechanism. In aspects of the invention, device modularity refers to the ability to arrange elements any modular manner, providing flexibility for different configurations and/or different functions of the device. Such elements or aspects can be used in apparatus, including for example, apparatus for pulmonary delivery of a composition.

Embodiments of the present invention comprise a multidose dry powder inhaler (DPI) and which is intended and designed for (but not limited to) use in asthma and COPD treatment.

The present invention relates to a blister strip inhaler which comprises a durable unit and a replaceable (cartridge) unit. In embodiments of the invention, the durable unit is intended to last for approximately one year and comprises an automatic blister opening mechanism, a priming mechanism, a breath-actuated trigger mechanism, and automatic dose counting mechanism (optionally, with lockout). In embodiments of the invention, electronics for providing user feedback are provided, and optionally, telehealth capability. The replaceable unit comprises a mouthpiece, blister strip, aerosol path, dose counter, a blister piercing assembly and aerosolization engine assembly. The lockout mechanism prevents further use of the cartridge when the dose counter reaches a preselected limit, such as zero.

The inhaler is supplied with appropriate mechanisms to enable "open-Inhale-close" functionality to assure reliability and ease of use by the patient. Additionally in some embodiments of the present invention both audible, such as by mechanical clicking, and visual, such as by LED signal lights, or audible warning tones, confirmation is provided of dosing and appropriate error messages are obtained (via the electronics or mechanical indicators) to alert the user if a dose was not properly obtained. In some embodiments only mechanical indicators are provided, and in some embodiments only electronically enabled indicators are provided.

Energy to drive the inhaler systems, and ultimately for piercing the blister (sometimes referred to as a receptacle) is generated by opening of a cap covering the mouthpiece. This energy is stored in an energy storage means, for example, a spring or other biasing means, and released to power the appropriate mechanisms as described herein. Opening of the cap thus constitutes a priming step (with associated mechanisms defining a priming mechanism) wherein a primary gear train is used to energize a spring. In embodiments of the invention, as the cap is opened energy is mechanically transmitted to a rack gear, via a series of gears comprising a primary gear train. The rack gear is pulled upward, that is, in the direction of the user of the device, and the rack gear transmits energy to the spring. When the cap is fully open, the spring is fully energized and the rack component engages a latch element, in turn disengaging the rack from the primary gear train. A breath actuated trigger mechanism senses patient inhalation and releases the latch element at the appropriate point, causing the spring to release stored energy and transmit the energy to an aerosolization engine. The aerosolization engine which further comprises piercing elements, translates linearly from a first to a second position, causing the blister to be pierced and permitting aerosolization to proceed. Following piercing, a biasing means, such as a spring, returns the aerosolization engine to its first position. In embodiments of the invention, the mechanisms designed and configured for latching and unlatching may be viewed as a subset of the priming mechanism.

Upon closing the cap, an indexing mechanism advances the blister strip through a series of gears. Part of the indexing mechanism resides in the durable unit and part in the replaceable unit or cartridge. If the blister is not pierced, the indexing mechanism does not engage thereby minimizing wasted doses.

In some embodiments, the inhaler device comprises electronics which are normally in a sleep state, but awakened, initiated or turned on, when the cap is opened. The device electronics sense if the mechanism is in a ready state, that is the device is primed and latched properly and ready for the patient inhalation. At this point, an inhalation will trigger or activate the mechanisms that unlatch the stored energy and pierce the blister. In some embodiments a pressure sensor or flow sensor is provided to detect pressure drop or flow change caused by inhalation, thus providing a means to monitor inhalation. Appropriate processing electronics/software can record various parameters respecting inhalation including time of inhalation, pressure drop, pressure drop over time and others. A visual signal means such as one or more LEDs may be supplied to provide alternative or additional user feedback including device ready to use, dose complete and error condition. Additionally or alternatively, audible and other human perceptible signal forms and formats can be employed to supply device condition state information to the user and/or also to convey or to supply information which may be unrelated to the state of the device, such as patient compliance, usage, and ambient condition information.

A blister strip is loaded within the cartridge and in embodiments contains 31 doses, each dose in its own sealed container. The blister strip is pulled through the device along a series of tracks. Once used, the blister strip is pushed back into the same tracks, thus conserving space resulting in a compact device.

An aerosol engine, comprising a double venturi arrangement provides for effective aerosolization of the powder dose within the dry powder inhaler, which can be achieved by exposing the dose agglomerates to lift and drag forces generated by a flow of air. The magnitude of these forces depends upon the difference achieved between the air velocity of the velocity of the agglomerate particles. A venturi architecture comprising a throat element and diffuser element is effective for achieving high peak flow velocities, and hence large aerosol forces, because the diffuser is able to recover a large proportion of the static pressure required to draw air through the throat. This allows the high peak flow velocities to be achieved whilst limiting the airway resistance. The double venturi, with two cones or divergent sections at the exit of the aerosolization engine, slows down the flow to help minimize oropharyngeal deposition and also permits a compact device.

A high resistance can be generated by a narrow throat, which for a given flow rate will tend to increase air velocities and hence increase aerosol forces. Also, a high resistance means that for a given pressure drop the flow rate is reduced and the maximum velocity of air exiting the device is thus lowered, which acts to decrease fine particle deposition in the patient's mouth. However, for some patients, a high resistance inhaler can make the inhaler device uncomfortable to use. Placing two otherwise high resistance venturi airways in parallel produces an overall resistance that is significantly lower than that for each of the airways individually, resulting in a device that is easier to use across a range of expected pressure drops, thus compatible with most patient's inhalation capabilities, such as between about 0.5 and 6 kPa, or between about 1 to 5 kPa, or between about 1.5 to 4.5 kPa.

In embodiments of the invention, an actuation mechanism is provided for providing a precise linear translation of a piercing or puncturing element for piercing a foil blister in response to a relatively coarse linear movement of an actuator, such as a button or lever. The actuation mechanism provides the accuracy required for piercing, independent of the nature of motion of the actuator. This mechanism also mitigates the need for extremely precise alignment of the actuating mechanism and the actuator, which simplifies an assembly process for the device. This configuration further beneficially allows for the actuation mechanism to be on one assembly, such as on the durable unit, and the piercing mechanism to be on another assembly, such as on the cartridge. The mechanism is preferably self-resetting so that it is always ready for the next actuation.

In embodiments of the invention, a dose counter is provided with a numerical readout to alert the patient to doses remaining. In some embodiments, the dose counter comprises concentric rings having spaced apart numerals which appear through a window in the cartridge. Various color schemes can be used to provide additional patient information such as color coding in red indicators nine to zero to reinforce the limited number of doses remaining and to remind the patient order a refill. A mechanical interlock is enabled upon the dose counter reaching zero thus preventing the empty cartridge from being used further.

The device is well-suited to inhalation formulations which make use of the Novartis PulmoSphere™ engineered particles, as well as lactose blends, and other inhalation formulations. While some embodiments are optimized for PulmoSphere™ engineered particle formulations, it is expected that delivery efficiency and efficacy will be improved irrespective of inhalation formulation used with the device. Exemplary engineered particle formulations may be found in U.S. Pat. Nos. 6,565,885, 7,871,598, 8,349,294 and 8,168,223.

In some aspects the invention comprises a multiple dose powder inhalation device comprising: a body comprising an interior cavity; and a cartridge that is removably insertable into the interior cavity of the body, the cartridge comprising a mouthpiece through which aerosolized powder medicament may be delivered to a user; wherein the cartridge houses a strip of receptacles, each receptacle adapted to contain a dose of powder medicament; a piercing mechanism and an aerosol engine, and wherein the body comprises a priming mechanism and a breath actuated mechanism that communicates with the strip of receptacles in the cartridge to selectively advance the strip of receptacles and wherein the body further comprises an actuator mechanism that communicates with the piercing mechanism in the cartridge to selectively cause the piercing mechanism to create one or more openings into a receptacle.

In some aspects the invention comprises a multiple dose powder inhalation device comprising: a body comprising an interior cavity; and a cartridge that is removably insertable into the interior cavity of the body, the cartridge comprising a mouthpiece through which aerosolized powder medicament may be delivered to a user; wherein the cartridge houses a strip of receptacles, each receptacle adapted to contain a dose of powder medicament, a dose counting mechanism, an automatic receptacle opening mechanism and an aerosol generating mechanism; and wherein the body comprises a cap that may be moved from a closed position that covers the mouthpiece on the cartridge to an open position that exposes the mouthpiece, wherein the movement of the cap to the open position stores energy in a spring, which then becomes latched in a biased position; and wherein the automatic receptacle opening mechanism comprises a breath-actuated mechanism disposed at least partially on the body that unlatches the biased spring to cause a receptacle to be pierced.

In some aspects, the invention comprises a multiple dose powder inhalation device comprising: a body comprising an interior cavity; and a cartridge that is removably insertable into the interior cavity of the body, the cartridge comprising a mouthpiece through which aerosolized powder medicament may be delivered to a user; wherein the cartridge houses a strip of receptacles, each receptacle adapted to contain a dose of powder medicament, a receptacle piercing mechanism and an aerosol generating mechanism; and wherein the aerosol generating mechanism comprises a double venturi with the venturis arranged in parallel with respect to the airflow direction.

In some aspects, the invention comprise a multiple dose powder inhalation device comprising: a body comprising an interior cavity; and a cartridge that is removably insertable into the interior cavity of the body, the cartridge comprising a mouthpiece through which aerosolized powder medicament may be delivered to a use; wherein the cartridge houses a strip of receptacles, each receptacle adapted to contain a dose of powder medicament, a piercing mechanism and an aerosol generating mechanism; wherein the body communicates with the cartridge to cause actuation of the piercing mechanism and/or to cause advancement of the strip of receptacles and wherein the body further comprises electronic circuitry which monitors that state of the mechanisms in the inhaler body and illuminates or activates feedback indicators in response to state changes in the mechanism.

In some aspects, the present invention comprises a multiple dose powder inhalation device comprising: a body comprising an interior cavity, a priming mechanism, a blister piercing actuator mechanism and a drive indexing mechanism; and a cartridge that is removably insertable into the interior cavity of the body, the cartridge comprising a mouthpiece through which aerosolized powder medicament may be delivered to a user; wherein the cartridge comprises a strip of receptacles, each receptacle adapted to contain a dose of powder medicament, the cartridge further comprises a receptacle piercing mechanism and an aerosol generating mechanism; wherein the body communicates with the cartridge to cause actuation of the piercing mechanism and to cause advancement of the strip of receptacles; and wherein the body further comprises electronic circuitry which monitors a state of the mechanisms in the inhaler body and illuminates feedback indicators in response to state changes in the mechanism.

In some aspects, the present invention comprises a multiple dose powder inhalation device comprising: a body comprising an interior cavity, a receptacle index mechanism, a priming mechanism, a latching and unlatching mechanism, a receptacle piercing drive mechanism; and a cartridge that is removably insertable into the interior cavity of the body, the cartridge comprising a mouthpiece through which aerosolized powder medicament may be delivered to a user, a receptacle piercing mechanism, a dose counter, a dose lockout mechanism, and an aerosol generating mechanism; wherein the cartridge comprises a strip of receptacles, each receptacle adapted to contain a dose of powder medicament; wherein the body communicates with the cartridge to cause actuation of the piercing mechanism and/or to cause advancement of the strip of receptacles; and wherein the cartridge lockout mechanism prevents further use of the cartridge under one or more predetermined conditions.

In some aspects, the present invention comprises a method of delivering by pulmonary administration a medicament in powder form, the method comprising: providing a multidose blister inhaler consisting of a first unit comprising a body comprising an openable cover mechanically coupled to a means for storing mechanical energy, an electronic inhalation sensing means, and a breath actuated mechanism for actuating the stored energy; and a second unit comprising a mouthpiece, a dose counting mechanism, an aerosolization engine comprising a piercing mechanism, an aerosol path, and a blister strip conveyance means and a blister strip comprising between 20 and 65 doses; and opening the cover, inhaling the medicament and closing the cover.

TERMS

"Medicament" is a drug used to diagnose, cure, treat, or prevent disease, referring to as a pharmaceutical drug, medicinal product, medicine, medication, etc.

The term respiratory tract includes the upper airways and lower airways. The upper airways or upper respiratory tract includes the nose and nasal passages, paranasal sinuses, the pharynx, and the portion of the larynx above the vocal cords. The lower airways or lower respiratory tract includes the portion of the larynx below the vocal cords, trachea, bronchi and bronchioles. The lungs can be included in the lower respiratory tract or as separate entity and include the respiratory bronchioles, alveolar ducts, alveolar sacs, and alveoli.

The term passive DPI refers to a powder inhaler that uses a patient's inspiratory effort to deagglomerate and disperse bulk powder into an aerosol. In contrast, an active DPI uses a mechanism in the apparatus as at least a portion of generator of the aerosol.

Terms of relative position as used herein, such as "upwards", "downwards", "vertical" etc. are, unless otherwise clear from context, interpreted with reference to the device as oriented by a user during an inhalation. Similarly, directions such as "clockwise" or "counterclockwise" are to be interpreted in the context of the Figure to which they refer.

DRAWINGS

These features, aspects, and advantages of the present invention will become better understood with regard to the following description, appended claims, and accompanying drawings which illustrate exemplary feature of the invention. However, it is to be understood that each of the features can be used in the invention in general, not merely in the context of the particular drawings, and the invention includes any combination of these features, where:

Figure 6:
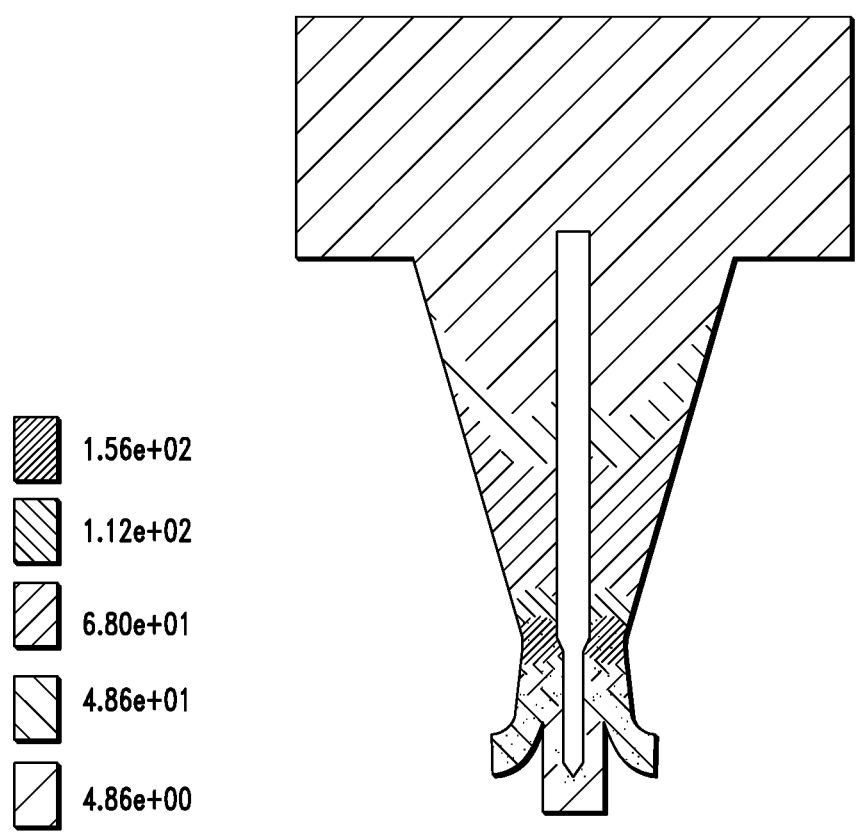

FIGS. 5a-5c comprise a cutaway view, a perspective view and a bottom view respectively of an embodiment of the aerosolization engine of the present invention FIG. 6 is an illustration showing results of computational fluid dynamics (CFD) analysis of an embodiment of the invention, showing airflow velocities in meters per second (m/s).

Figure 7:
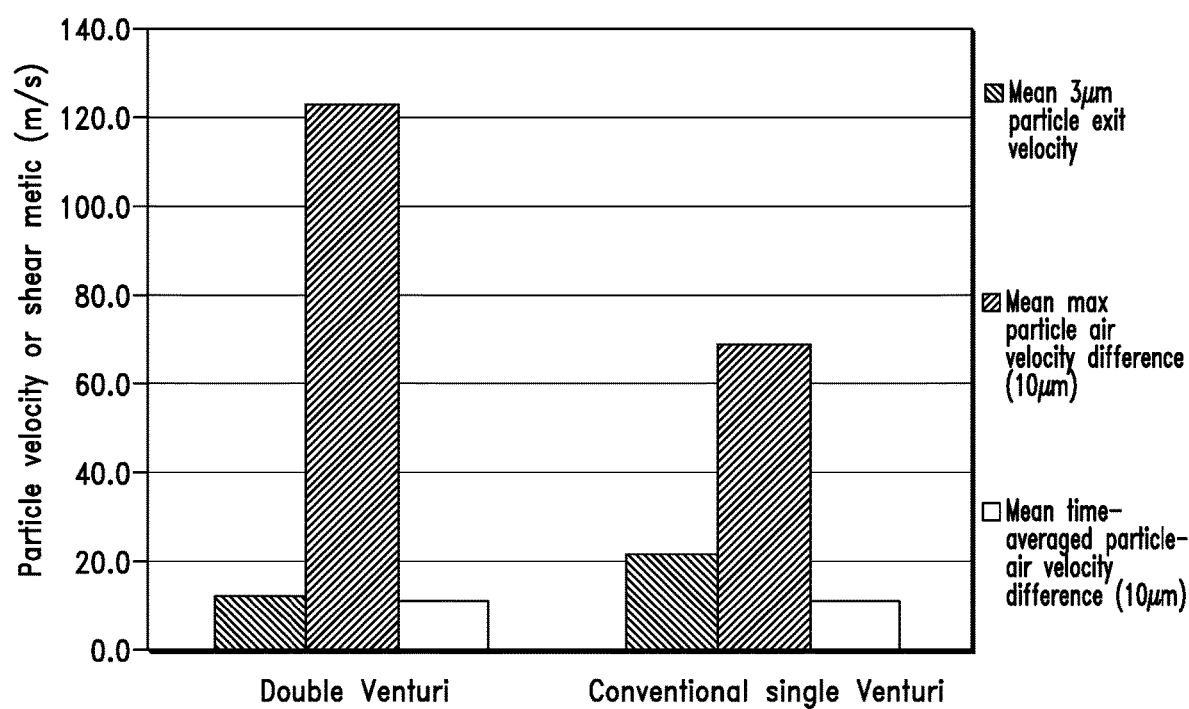

FIG. 7 is a graph showing particle tracking results comparing the resultant particle velocities of embodiments of the present invention to those obtained using a conventional venturi.

Figure 8:
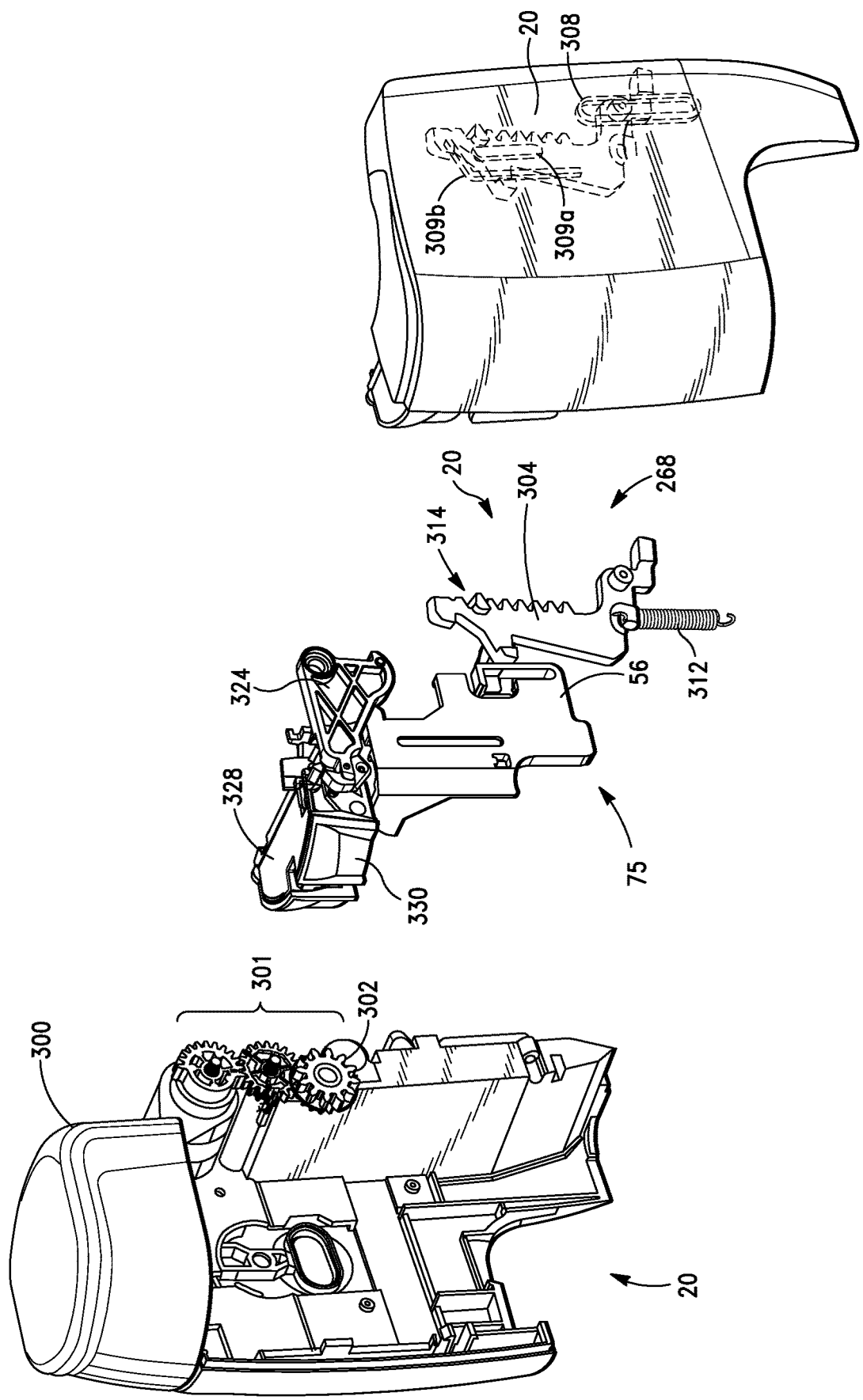

FIG. 8 is a drawing showing elements of a priming system comprising part of an automatic blister opening system according to an embodiment of the present invention.

FIGS. 9a-9d show elements of a breath actuated trigger mechanism comprising part of an automatic blister opening system according to an embodiment of the present invention. The breath actuated trigger mechanism is sometimes referred to as a breath actuated mechanism, or BAM.

FIGS. 10a-10c illustrate components in various stages of operation of a dose counting system according to embodiments of the present invention.

Figure 11:
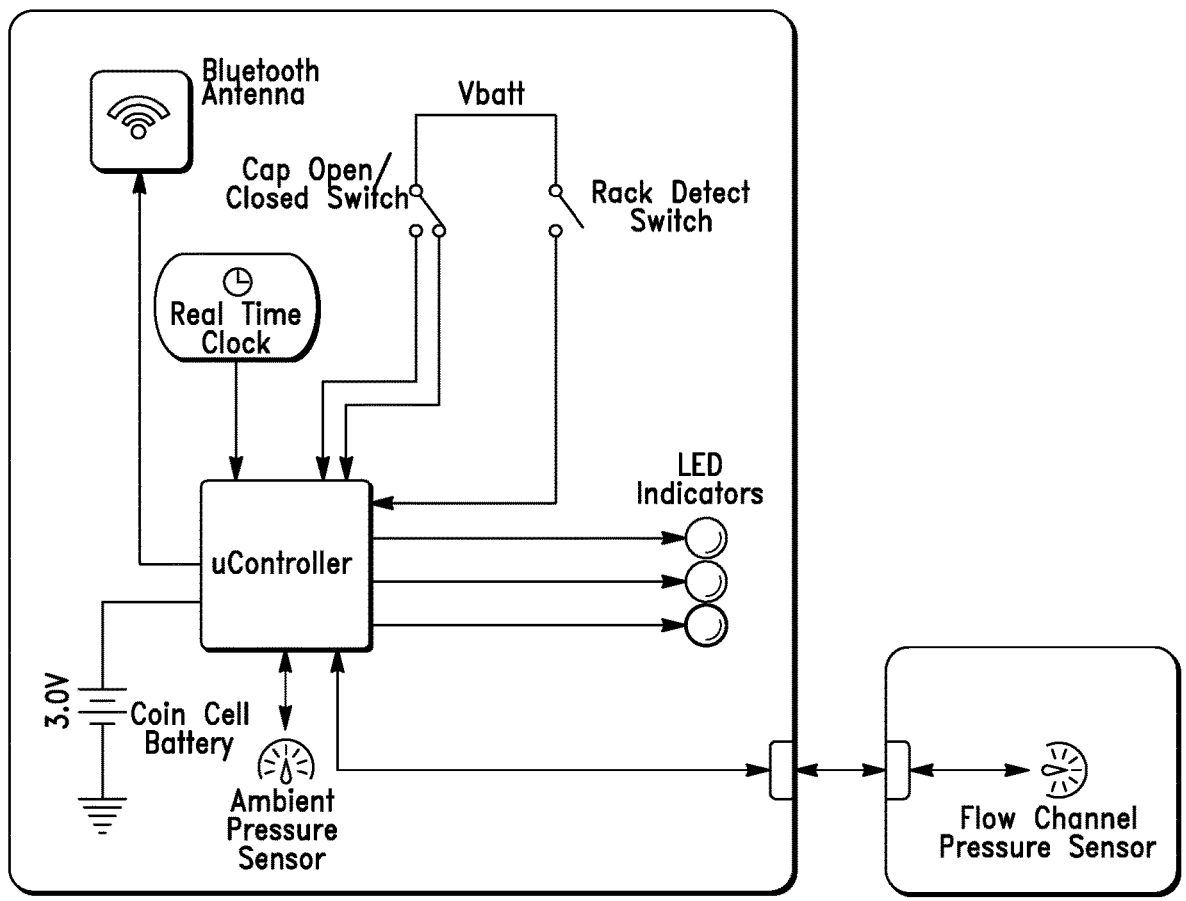

FIG. 11 is an exemplary circuit schematic of device electronics.

Figure 12:
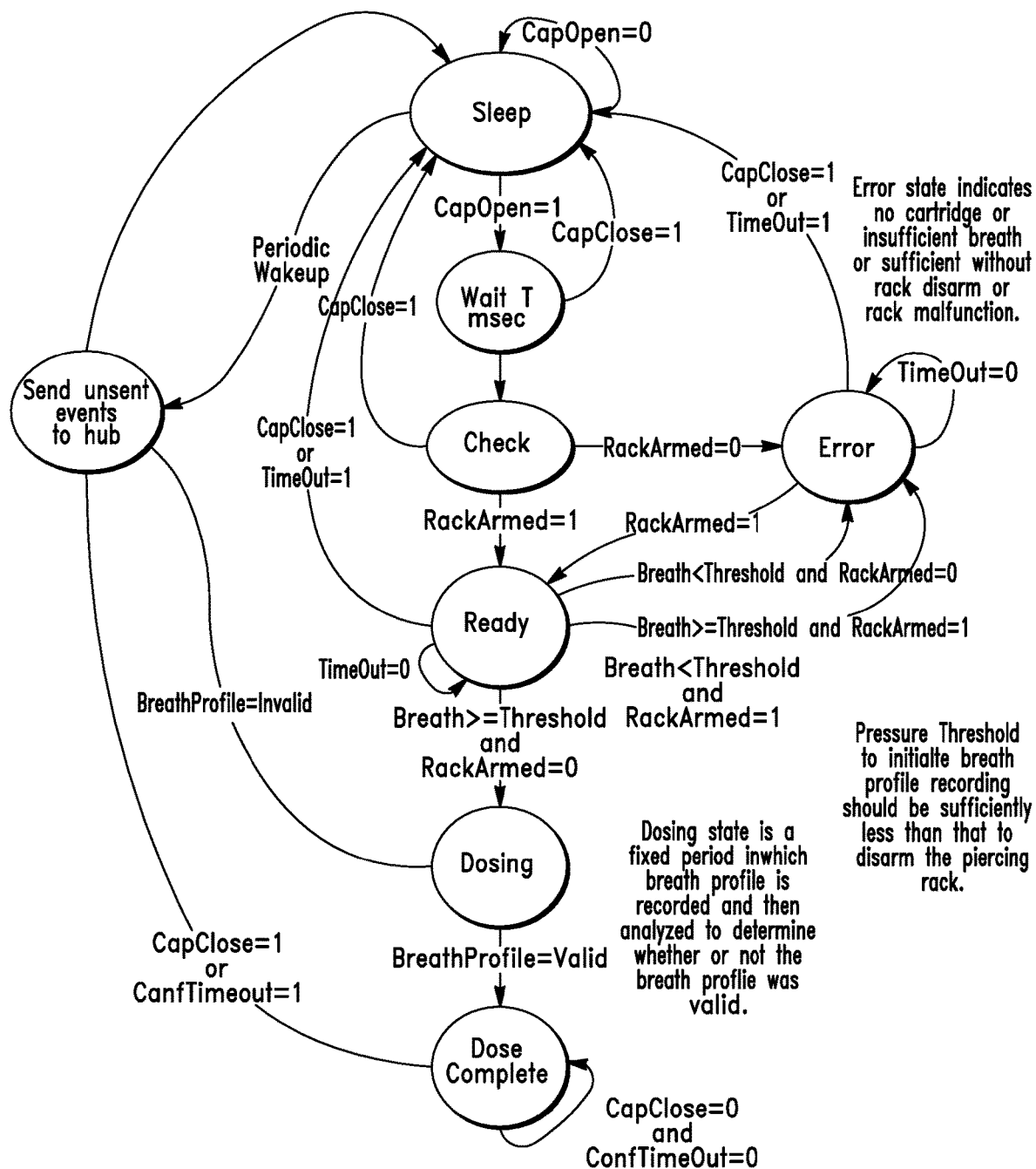

FIG. 12 is an exemplary software state diagram illustrating possible user messages.

Figure 13:
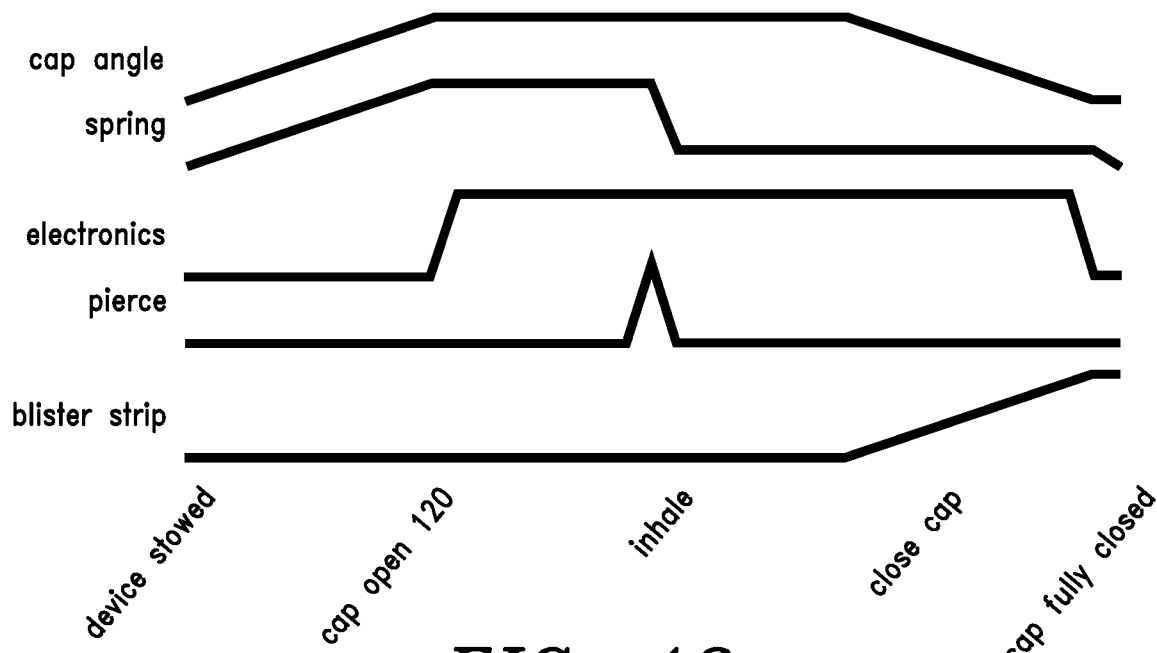

FIG. 13 is a device state graph showing elements of the device at certain time points along an operational cycle.

Figure 14:
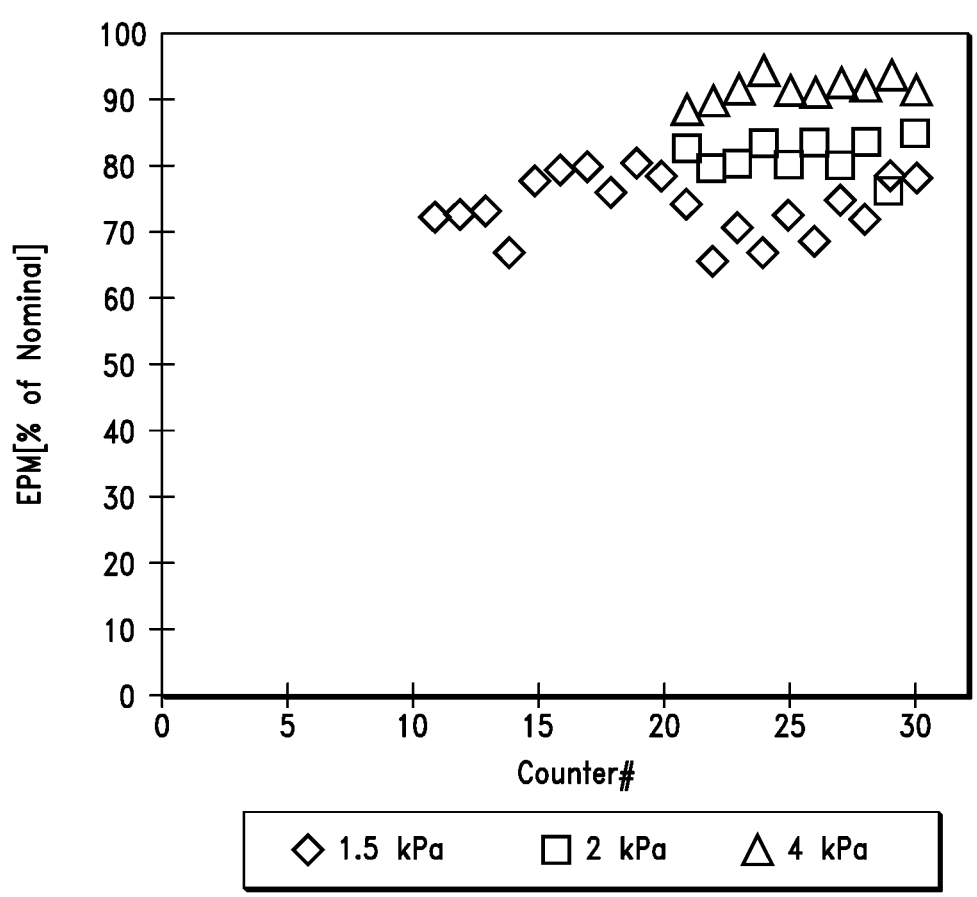

FIG. 14 is a graph of emitted dose versus blister number for three different inspiratory pressure drops, using a device according to embodiments of the present invention.

Figure 15:
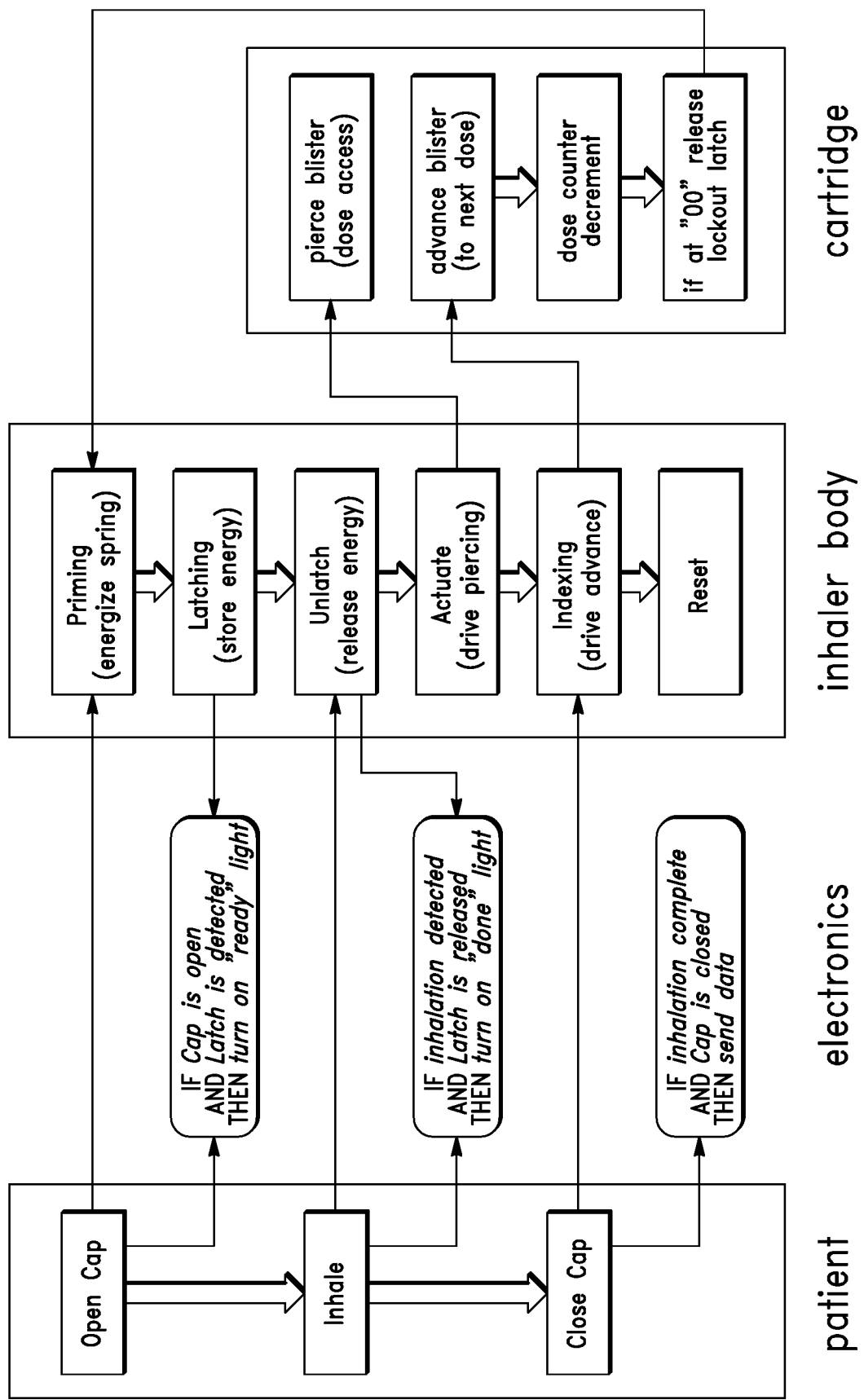

FIG. 15 is a block schematic showing relationships and disposition of certain systems and subsystems of the inhaler.

DETAILED DESCRIPTION

The following description is made for the purpose of illustrating the general principles of the present invention and is not meant to limit the inventive concepts claimed herein.

Further, particular features described herein can be used in combination with other described features in each of the various possible combinations and permutations.

Unless otherwise specifically defined herein, all terms are to be given their broadest possible interpretation including meanings implied from the specification as well as meanings understood by those skilled in the art and/or as defined in dictionaries, treatises, etc.

It must also be noted that, as used in the specification and the appended claims, the singular forms "a", "an", and "the" include plural unless otherwise specified.

In embodiments of the invention, the mechanical systems can be viewed as separate but interrelated subsystems. Thus in one embodiment, a subsystem comprises a priming mechanism, which is the mechanism that initially energizes a mechanical energy storage component, such as a spring. In embodiments of the invention, energy is stored in a spring when a user opens a cap or cover, covering a patient interface end or mouthpiece portion of the inhaler device. In embodiments of the invention, the priming system comprises a cap, priming gear train, pivoting rack, guiding tracks and main spring.

In another system in an embodiment of the invention there is provided a breath actuated trigger mechanism, which is a mechanism designed to retain mechanical energy supplied by a spring, and to releases the mechanical energy upon patient inhalation. The system comprises elements of a pivoting rack, a link bar, and air flap, and an airbox.

In another system, in embodiments of the invention there is provided blister puncturing or piercing mechanism, which is the mechanism that uses stored energy (for example from the spring) to pierce the blister and thereby make the contents available for patient inhalation. This blister piercing system comprises elements of a main spring, a rack gear, an actuator arm, a mouthpiece subassembly, specifically configured cam, a piercing arm, and an aerosol engine.

In some embodiments of the present invention, there is an automatic blister opening mechanism, which is designed and configured to automatically open the blister when the patient inhales. This automatic blister opening mechanism in some embodiments, comprises a collection of the priming mechanism system, the breath actuated trigger mechanism, and the blister piercing mechanism.

It is noted that the systems and subsystems described above and hereinafter are described as such for convenience and to improve understanding of the elements and features of the invention, but are not intended to be limiting and that various combinations and permutations of these systems, subsystems and individual elements are contemplated to be within the scope of the present invention.

Modularity

The Inhaler is a multi-dose dry-powder inhaler consisting of two main assemblies: an Inhaler body (sometimes referred to as a "durable unit or portion") and a replaceable cartridge (sometime referred to as a "cartridge" or "replaceable unit or portion"). In embodiments of the invention, the cartridge holds up to thirty-one doses of medication contained in a foil-foil blister strip, corresponding to one month of usage for a once-a-day therapy. When all the doses in the strip have been used, the cartridge can be removed from the inhaler body and replaced. Blisters contemplated for use with the present invention comprise a foil tub configuration on a foil strip, however the invention is not so limited. Exemplary blisters and blister strips are well known to the art, and disclosed generally in co-pending US Patent Application Publication US2015-0090262, filed 25 Sep. 2014, and assigned to the same assignee of the present invention.

In embodiments of the present invention, the inhaler body has a useful life of at least one year.

FIGS. 1a-1f show the inhaler device of the present invention referred to by the general reference character 10. The inhaler 10 comprises the inhaler body 20 and cartridge 30. The medication in the inhaler device is contained in a blister strip 40 comprising a series of individually sealed doses within blister tubs (or simply "blisters") 42 (shown in FIG.

3). The dosing sequence first requires small holes to be punched in the blister foil to gain access to the powder. In embodiments of the invention, the holes may be 0.5 to 2 mm in diameter such as 1 mm in diameter. The energy of the patient's inhalation is sufficient to evacuate the powder from the blister tub 42. At the end of the dose, the blister strip 40 is advanced to the next blister tub 42 to prepare for the next dose.

Figure 1A:
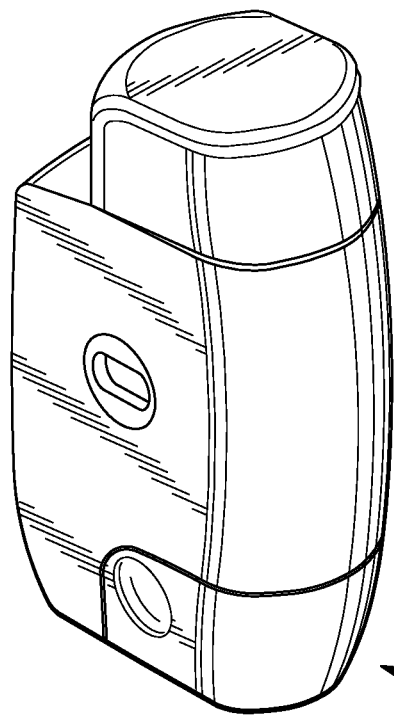
FIGS. 1a-1f are various perspective views of an exemplary embodiment of the inhaler device of the present invention as: assembled inhaler, body or durable unit, and cartridge.
Figure 1B:
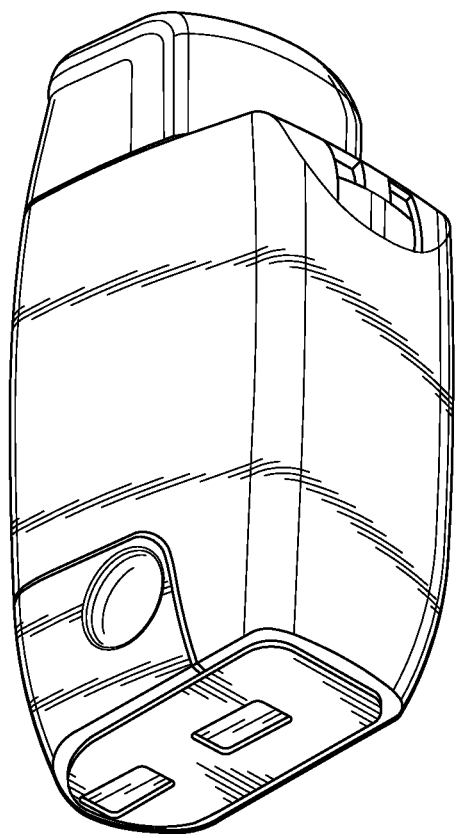
Figure 1C:
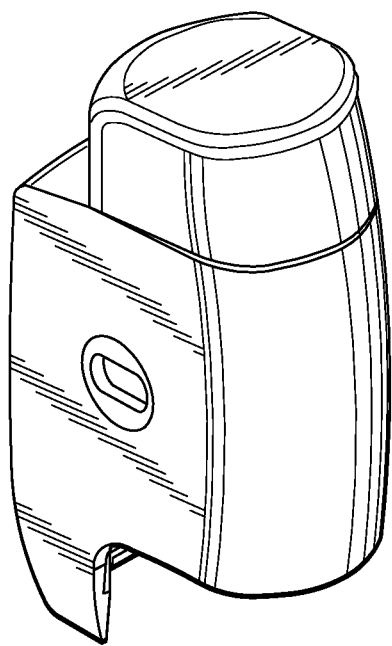
Figure 1D:
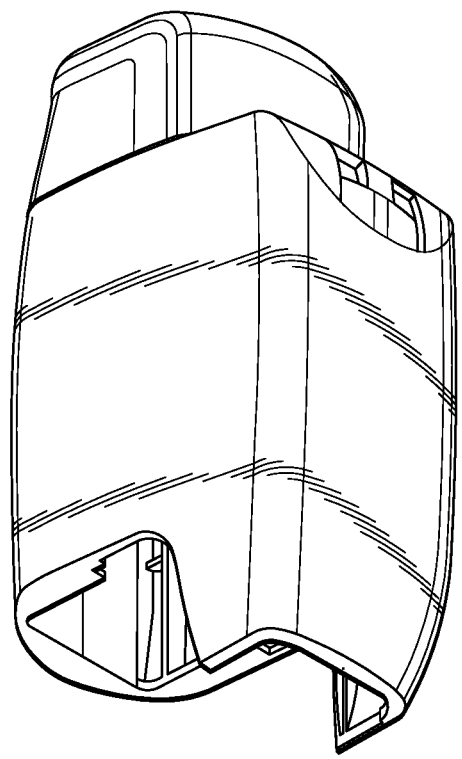
Figure 1E:
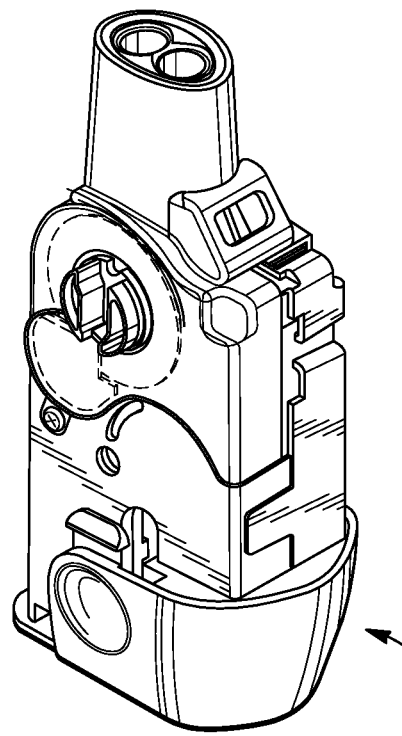
Figure 1F:
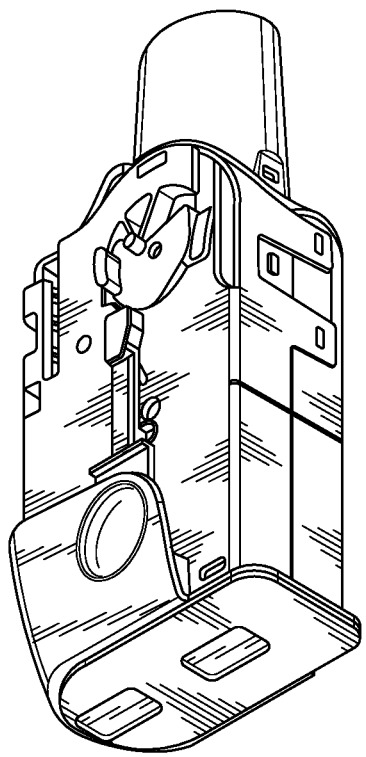
Figure 2:
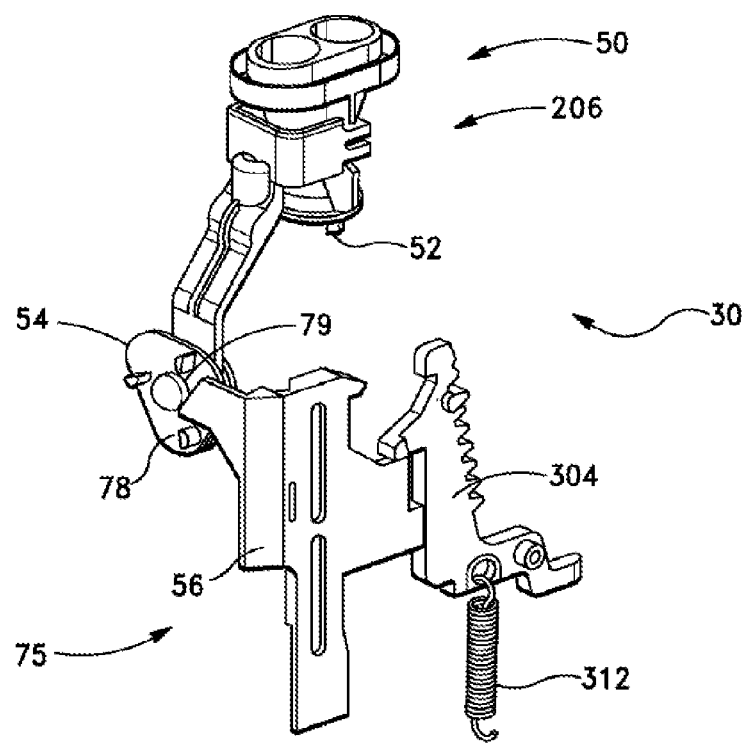
FIG. 2 is an exemplary illustration of components comprising an automatic blister opening system according to an embodiment of the inhaler device of the present invention.

The cartridge 30 contains all of the elements necessary for drug delivery. In embodiments of the present invention, the cartridge 30 may not contain the mechanisms needed to drive those elements during the dosing sequence; such mechanisms may be partially in the body 20 and partially in the cartridge 30. Referring to FIG. 2, the cartridge 30 contains an aerosol engine 50 having a plurality of piercing elements 52 and a cam 54 to precisely control motion of the piercing elements and thereby enable it to puncture a blister foil about a top surface thereof to enable escape and aerosolization of powder contents therein. In some embodiments three piercing elements 52 are provided to make the three holes in the blister foil. The cam 54 does not move until it is driven by an actuator arm or lever 56 that resides in the body 20 (note that in FIG. 2 the actuator arm 56 appears in connection with the cartridge 30, but it is actually located, as shown in other Figures, on body 20). Likewise, the blister strip 40 is guided by a series of tracks 44 and is engaged with a drive or index wheel 46, all within the cartridge. However, the index wheel does not move the blister strip until mechanisms in the body 10 drive the wheel at the appropriate time. Thus, there are two main mechanical interfaces between the body and the cartridge: actuation of the piercing cam and driving of the blister advance mechanism.

In embodiments of the present invention, there are other possible designs that could be used to allow the body 20 to generate the mechanical inputs to the cartridge 30. For example, the mechanism that drives the piercing cam in the cartridge could be the pressing of a button on the inhaler body 20, or a more elaborate breath-actuated latch that releases stored spring energy to drive the cam, or even an electronically powered actuator such as a solenoid. All of these mechanisms are different ways to perform the same function, that is, translating an element by a set distance to drive the piercing cam in the cartridge. Hence, in aspects of the invention, these mechanisms would appear the same to the cartridge, and would therefore be interchangeable as far as user experience and delivery of the dose is concerned.

In addition to the mechanisms that interface with the cartridge, there are a number of ways that the inhaler body could provide feedback of correct operation to the patient. In embodiments of the present invention, the feedback mechanisms monitor the state of the mechanisms in the inhaler body, and/or may communicate information to the user, but do not influence the behavior of those mechanisms. Therefore, the choice of which feedback mechanism to implement has no effect on the aerosol delivery from the device.

A variety of feedback indicators could be integrated with the Inhaler body. In embodiments of the invention, a mechanical flag just above the dose counter changes color (e.g. white to green) to signify that the device has been operated correctly, i.e. the patient has properly operated the device to receive the dose. These feedback indicators could comprise simple tactile or audible feedback, or a mechanical flag that changes position, or could be more elaborate with the inclusion of electronics to monitor the operation of the device and illuminate a light or series of lights. In embodiments of the invention, the mechanical flag may be a user perceptible signal, such as a colored portion of a visible gear, which confirms to the user the gear rotation after inhalation. Again, as long as these indicators do not change the mechanical inputs from the Inhaler body to the cartridge, the delivery of the dose is not affected.

As noted above, in embodiments of the present invention the Inhaler device comprises modules. One module comprises the cartridge, which contains all the elements that are essential to control the aerosol delivery of the device. Another module comprises the inhaler body, and it provides the user interface for the device and has mechanisms to drive the piercing and blister advance mechanisms in the cartridge. Yet another module is the electronic circuitry, which monitors the state of the mechanisms in the inhaler body and illuminates feedback indicators in response to state changes in the mechanism. As long as the interfaces between the modules remain substantially consistent, changes within each individual module are functionally equivalent for the system, and to the patient or user of the device.

In embodiments of the invention, a benefit of this modularity is the fact that the aerosol delivery is determined by elements entirely within one of those modules, and is unaffected by changes in the other modules. Similarly, changes to details of each module are functionally equivalent provided they do not change the interfaces to the adjacent modules. This provides potential advantages in drug product registration, as adding new Inhaler body modules, or new features to existing modules, would likely not require additional clinical studies to prove that drug delivery is unaffected. Accordingly, in embodiments of the invention there is provided an inhaler and at least one medicament containing cartridge, together with instructions for use (such as a package information leaflet) which directs the user to insert the cartridge into the inhaler device, and operate the device by opening the cap, inhaling and closing the cap.

Aerosolization Engine

Figure 4:
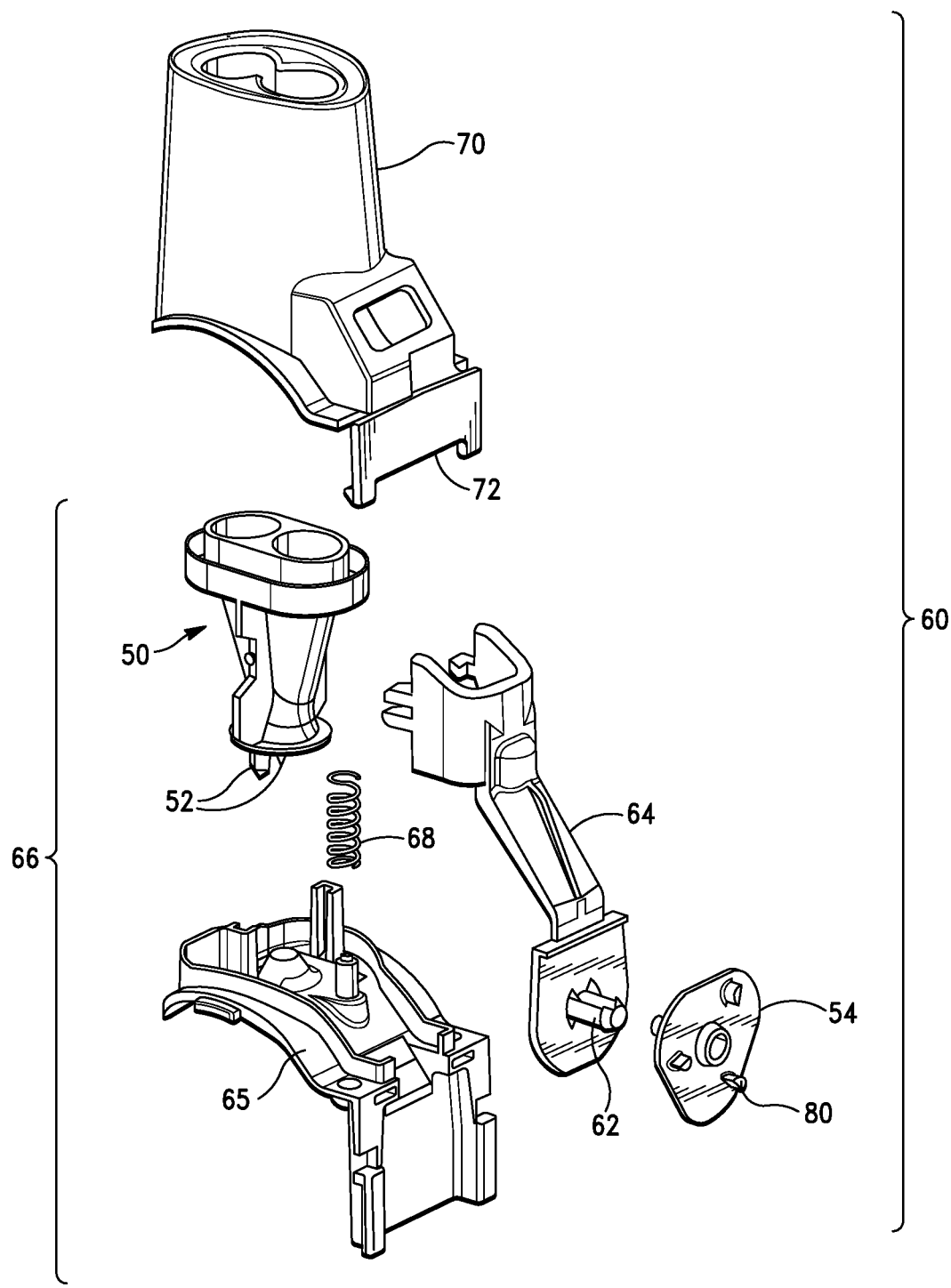
FIG. 4 is a partially exploded view of an embodiment of the present invention showing details of an aerosol engine and automatic blister opening system.

Referring to FIG. 4, there is shown the aerosol engine 50, which functions to both evacuate (or withdraw) powder from the blister 42, as well as to deagglomerate the powder contained therein and further to fluidize and aerosolize the powder for delivery to a patient. The aerosol engine 50 is, in some embodiments, a single molded component that provides both a means to pierce a foil lidstock of the blister strip, and structural elements or features to direct airflow to extract and deagglomerate powder from each blister. The piercing of the foil laminate occurs by translating the aerosol engine vertically (in some embodiments by approximately two mm) and then retracting it back to its first or original (starting) position. Upon the translation of the aerosol engine, three sharp protrusions comprising puncturing elements 52 on the bottom of the aerosol engine 50 create three corresponding openings in the lidstock of the blister 42. In some embodiments, the puncturing elements 52 are diamond shaped, however a variety of shapes are contemplated and within the scope of the present invention.

A pierce and retract mechanism 60 is used to drive and control the translation of the aerosol engine 50. This mechanism consists of the three-lobed cam 54 that attaches to an axle 62 on a cam arm 64. Cam arm 64 is movably attached to a feed plate 65, so that it may translate vertically. The aerosol engine 50, is in turn, mechanically coupled to the cam arm 64. The cam, cam arm and aerosol engine 50, together with a biasing spring 68 form a blister piercing assembly 66. The pierce and retract mechanism 60 comprises all the elements of the blister piercing assembly 66, plus the spring 68 and feed plate 65. The spring 68 biases the assembly 66 upwards (toward the mouthpiece 70) and is constrained in its upward motion by a stop (not shown) within the mouthpiece 70 which acts upon an upper surface of the aerosol engine 50.

The cam arm 64 and aerosol engine 50 are mechanically coupled so that they move up and down (vertically) in unison. The cam 54 is retained on the axle 62 of the cam arm 64 and can spin freely around this axle. A spring 68 biases the blister piercing assembly 66 upwards against a mouthpiece 70. A fixed flat surface 72 on the mouthpiece provides a bearing surface for the cam 54. As the cam spins, it rides against the flat surface on the mouthpiece 70 and pulls the arm 64 downwards by the desired distance, such as one to three mm.

The shape of the cam 54 determines the travel of the aerosol engine 50, and the travel of the aerosol engine 50 is selected to ensure a complete and consistent receptacle pierce. In embodiments of the invention, the cam 54 has three identical lobes that are positioned at the vertices of an equilateral triangle. Normally, the aerosol engine 50 is biased upwards against the mouthpiece 70 by the spring 68. In this position, two of the lobes of the cam 54 are resting against the bearing surface 72 of the mouthpiece. As the cam 54 is rotated, one of the cam lobes slides against the bearing surface 72 and the molded arm 64 is pushed downwards. The maximum downward travel of the assembly 66 occurs when the lobe of the cam 54 is directly above the axle 62 on the cam arm 64—a metastable state known as "dead center". Once the cam 54 rotates past dead center, the spring 68 drives the assembly upwards until it can achieve a stable condition, which is when two of the cam lobes contact the bearing surface 72 on the mouthpiece 70. Thus, a complete pierce and retract cycle occurs when the cam is rotated 120 degrees.

In the inhaler device 10 (and referring to FIGS. 2 and 8) components of an automatic blister opening mechanism 75 translate the actuator arm 56 by a preselected distance (for example nine to fifteen mm, such as ten to thirteen mm) in response to the patient's inhalation through the device. The tolerances of the resulting piercing motion are determined largely by the cam 54, and not by the actuator, which makes the motion easier to control. Thus, in embodiments of the invention, the actuator arm 56 is the only subsystem that is separate and separable from the subsystem containing the piercing elements. Thus the position of the actuator arm can vary slightly with respect to the piercing cam due to manufacturing tolerances, or to minor misalignments of the two subsystems. The movement of the actuator arm 56 is longer than necessary to ensure the piercing cam is driven by the correct amount of throw or displacement, even if the two subsystems are not perfectly aligned. The piercing mechanism requires more precise movement to create consistent openings in the blister. This precise movement is determined largely by the cam 54 which resides in the same subsystem as the piercing element 52. The tolerances between the cam and piercing element can be controlled to a much greater degree of precision. The cam 54 may have three substantially similar or identical driving posts 80, arranged similarly to the cam lobes on the vertices of an equilateral triangle, but rotated with respect to the cam triangle. When the actuator arm 56 is translated downwards, a driving surface 78 on the actuator arm 56 contacts one of the driving posts 80 and pushes it downwards (see FIG. 2). The downward force on the driving post causes the cam to rotate. Once the cam 54 has reached dead center, the bias spring 68 completes the rotation of the cam through the 120 degrees utilized in some embodiments for a full pierce-and-retract.

Since a full cycle of the pierce and retract mechanism 60 involves a pierce-and-retract of the aerosol engine 50, the three-lobed cam 54 mechanism ends up at the same state as when it started. The reset of the actuator arm 56 can be driven by a reset spring (not shown), and reset can be immediate or can be delayed until some other event occurs (e.g. the closing of a cap). This delay may be utilized to ensure the dosing cycle is complete (including mechanism reset) before initiating the next dose. Driving surface 78 on the actuator arm 56 is provided to nudge past the driving post 80 on the cam 54, which causes the cam to rotate slightly backwards, but not enough to cause the piercing elements of the aerosol engine to contact the blister. Thus, the reset of the mechanism is essentially automatic.

An advantage of the design is its suitability for either manual or automatic actuation. This flexibility in the actuation also allows the mechanism to be easily split apart at an interface between actuator arm 56 and cam 54, as either an aid assembly, or to facilitate a cartridge-based system with the a plurality of blisters 42 and the pierce and retreat mechanism 60 on the cartridge 30 and wherein the actuator arm 56 is present on the durable unit 20.

Although the cam 54 shown has three lobes to form an equilateral triangle, the same concept could have two, four, or more lobes. The cam throw is determined by the difference in radius of the inscribed and circumscribed circles on the polygon described by the cam lobes (in the case of a two-lobed system, it would be the difference between the half the thickness of the cam and half its length). As the number of lobes increases, the overall size of the cam gets larger for any given cam throw. While a two-lobe cam is theoretically the smallest, the geometry may be less favorable for a rotary motion with minimal force. Thus, in some embodiments, the three-lobed cam 54 is preferred.

As a result of the designing configuration of the pierce and retreat mechanism 60, a precise linear cam movement is advantageously derived from a separate coarse movement of an actuator for the purpose of piercing a foil blister. The tolerances are controlled by the cam 54, so the actuator can be on a separate assembly without adversely affecting the precision of the piercing motion. This beneficially achieves a reliable and precise piercing of the foil blister. In many embodiments, the piercing mechanism is compatible with (and/or a subset of) automatic blister opening mechanism 75 e.g. breath-actuated triggering of dose access. The nature of the aerosol path (shown in FIG. 5) is such that the openings in the blister made by the piercing elements 52 are unimpeded since once the mechanism 60 pierces the blister it then retracts out of the blister. This means that the aerosol path is un-impeded, however it also means that the tolerances of the piercing elements 52 and their motion upon entering the blister, and the position of the resultant punches above the blister during dose delivery should be precisely controlled to ensure optimal aerosolization and delivery of powder contents of the blister.

A further aspect of the present invention comprises the aerosol engine 50, also sometimes referred to as a deagglomeration engine for the inhaler 10. The aerosol engine 50 uses a combination of two venturi geometries in parallel to generate increased air velocities in a throat region of the aerosol engine 50 (compared to a single venturi engine). This increases the performance of the inhaler by exposing agglomerate particles to greater deagglomerating shear forces. Additionally, a maximum velocity at which the fine particles exit the inhaler is reduced when compared to a single venturi engine of the same overall length. This increases the performance of the inhaler by reducing the tendency for fine particle deposition on the throat and tongue of the patient and increasing the proportion of the dose that reaches deep into the lung.

An embodiment of a double-venturi configuration 100 is shown schematically in FIGS. 5a-5b. The double-venturi configuration comprises a first venturi 102 and a second venturi 104. Each of the venturis has a convergent section 106 and a divergent section 108. Each convergent section 106 has a minimum aperture, a maximum aperture, and an axial length L1 while each divergent section has a minimum aperture, a maximum aperture, and an axial length L2. The convergent and divergent sections 106 and 108 are arranged so that the minimum apertures of each convergent and divergent section abut to form a throat 110. Each divergent and convergent section is generally conically shaped. A maximum aperture of each of the convergent sections 106 collectively define an air inlet 112, and the maximum aperture of each divergent section defines an air outlet 114. The first and second venturis 102 and 104 are disposed such that there is a central axis A intermediate to the first and second venturis. Each of the convergent and divergent sections and throat define an airway through which inhalation powder, comprising particulates 118, which may be individual particles or in some circumstances agglomerates of fine or nanoparticles, travel from the air inlet and are dispensed through the air outlet.

In one version, each airway of the double-venturi configuration 100 gradually decreases in volume from the air inlet towards the throat and the each airway gradually increases in volume from the throat towards the air outlet. Each airway is selectively configured to be parallel to one other along the central axis. Operatively, each venturi can be generally circular in cross-section. Additionally, each of the airways in the throat is selectively configured to be identical in cross-section.

In another version, convergent sections of the double-venturi configuration integrate into a central convergent section. The central convergent section is configured to be generally circular in cross-section. In another version, the airway in each convergent section could merge into a central airway.

The aerosol engine 50 further includes receptacle puncturing elements 52. In embodiments of the invention, there is a first and a second receptacle puncturing element 52, operatively connected to the convergent section and parallel to but displaced from the central axis A. A third receptacle puncturing element is configured to be arranged about the central axis A. Each receptacle puncturing element 52 comprises a blade or piercing element.

In one version, each airway of the aerosol engine 50 gradually decreases in volume from the air inlet towards the throat and the each airway gradually increases in volume from the throat towards the air outlet. Each airway is configured to be generally parallel to each other along the central axis. Operatively, each venturi can be generally circular in cross-section. The convergent sections of the venturis are proximal to the blister or receptacle 42, while the venturi divergent sections are proximal to the mouthpiece 70.

It is understood that more than two venturis can be configured to realize the same function as the two venturi configuration 100. Also in the context of the inhaler 10, or generally, a device for dispensing inhalation particulates, other configurations of the aerosol engine 50 are possible, including a single venturi, or multiple venturi combinations, for example, a triple venturi.

One schematic perspective view of the aerosol engine 50 is shown in FIG. 5b. While various overall lengths of the aerosol engine 50, convergent sections 106 and divergent sections 108 may be implemented, in one embodiment the aerosol engine 50 is no more than about twenty-five (25) mm along the central axis A, as measured from a bottom of the air inlet 112 end to a top of the air outlet end 114. In some embodiments, overall dimensions of aerosol engine 50 are no more than about twenty-five mm in length, no more than about twenty mm wide and no more than about twelve mm deep. These dimensions are advantageous in that the relatively short overall length of the aerosol engine results in a relatively short airflow path, which contributes to compactness of the entire inhaler device 10, while maintaining good powder deagglomeration and/or fluidization and/or aerosolization properties. The short airflow path also helps to minimize unwanted powder deposition within the device. Moreover, it is an advantage that by using multiple venturis, appropriate fluidization and deagglomeration forces are applied to optimize inhalation particle delivery to the target sites within the lung.

FIG. 5c is a schematic bottom view of the aerosol engine 50. Whilst not limited to specific dimensions, in one embodiment a width of the air inlet 112 is between about twelve and seventeen mm. Similarly, a diameter of each of each throat 110 may be about one to two mm. The airways in the throat 110 can be identical, or selectively different in size and/or shape.

CFD analysis of the aerosol engine 50 has shown that an air velocity of each airway in the convergent section is rapidly accelerated from the inlet to the throat. After a high air velocity, such as about 80 to 120 m/s, is generated in each throat of the airway the air velocity of each airway is subsequently decelerated to about 10 to 30 m/s from the throat to the outlet by the divergent sections of the invention.

CFD particle tracking (comprising particle-air velocity differences) of nominal 10 μm diameter agglomerate indicates that agglomerate particles (which a dry powder drug formulation may contain) are exposed to high aerosol forces in the throats and throughout the diffusers of the airway. The particle-air velocity difference indicates that agglomerate particles are exposed to high aerosol forces in the throat and throughout the diffusers of aerosol engine 50. See FIGS. 6 and 7.

Placing two high resistance venturi airways in parallel within the invention produces an overall resistance that is significantly lower than each of the airways individually. This is shown by Equation 1, where $R_{parallel}$ is the combined resistance of $R_1$ and $R_2$ in parallel. Therefore, the advantages of the high resistance geometry which generates the high peak flow velocities for smaller particles and better lung deposition can be maintained, whilst the overall resistance of the invention is lowered which provides the patient experiences with a comfortable device resistance.

$$R_{parallel} = \frac{1}{\frac{1}{R_1} + \frac{1}{R_2}} \qquad \text{Equation 1}$$

Particle tracking results comparing embodiments of the present invention with a conventional venturi is shown in FIG. 8. A direct comparison of a conventional single venturi and a double venturi arrangement according to embodiments of the invention with equal length and resistance has been carried out using CFD. As illustrated by FIG. 8, a mean exit velocity for a 3 μm particle from the aerosolization engine according to embodiments of the present invention is about 12.0 m/s while that the prior art single venturi is about 22.0 m/s. Similarly, a mean time average particle air velocity difference for a 10 μm particle is about 11.0 m/s whereas that of the single venturi is almost the same. A mean maximum particle air velocity difference (for a 10 μm particle) of an embodiment of the present invention is about 122.0 m/s while that of the single venturi is about 68.0 m/s. This quantifies an advantage of the invention in terms of achieving a greater maximum particle-air velocity difference for 10 μm agglomerates, which is indicative of improved aerosol performance. In other words, the aerosol engine of the present invention achieves a greater deagglomeration compared to a prior art single venturi aerosol engine, while also resulting in smaller particle exit velocity. This means better deagglomeration and lower unwanted tongue and throat deposition.

Referring again to FIG. 5, a generalized device for dispensing inhalation particulates (not shown) comprises a feed plate 150 and aerosol engine 50. The feed plate 150 further comprises a feed tube 152, a bypass annulus 154, and a cone element 155 that is positioned relative to the aerosol engine 50 in the air inlet 112 to result in the formation of the bypass annulus 154. The bypass annulus 154 comprises an aperture around the feed tube 152 through which non-particulate carrying air may flow into the venturis 102 and 104. In other words, this air is bypass air which does not pass through the blister 42. The aerosol engine 50 is positioned about the feed plate 150 such that inhalation particles can only pass through the feed tube 152 from a storage portion 156 (for example a blister 42) containing inhalation particles into the airway. Refer to the arrows in FIG. 5a showing how intake air is divided into aerosolization air (directed into the storage portion 156) and bypass air (directed into the air inlet 112). In each convergent section air without inhalation particles can only pass through the bypass annulus 154 into the airway in each of convergent section 106. The storage portion 156 selectively comprises a storage outlet through which particulates can exit the storage portion into the feed tube 152. The storage portion can be any form of packaging such as blister 42, blister strip 40, bag, double aluminum foil (soft or hard), etc.

In many embodiments, the storage portion 156 (e.g. blister 42) with which the inhaler 10 is designed to operate may have a fill mass of 0.5 to 10 milligrams. In embodiments of the invention, a fill mass is 1 to 5 milligrams, such as 1 to 3 milligrams in particular when the formulation to be delivered comprises an engineered powder.

In one version of the invention, a center-disposed powder receptacle puncturing elements 52 is axially aligned with the feed tube while the blade or piercing element thereof descends into, then retracts from the storage portion, such that an outlet is formed in the storage portion through which aerosolized powder is withdrawn or extracted.

In embodiments of the present invention, there is provided generally a method for dispensing inhalation particles from an inhaler device, employing the aerosolization engine according to embodiments of the present invention. In embodiments of the present invention, the inhaler device suitably may be as set forth in this specification, comprising a feed plate and an aerosol engine. The aerosol engine is suitably aerosol engine 50. The feed plate is suitably feed plate 150. The aerosol engine may be coupled to the feed plate such that inhalation particles can only pass through the feed tube from a storage portion (for example a blister) for containing inhalation particles into the airway in each convergent section and air without inhalation particles can only pass through the bypass annulus into the airway in each convergent section. The method therefore comprises the steps of:

i) coupling the storage portion onto the feed plate;
ii) manipulating a puncturing element or a plurality of puncturing elements to pierce the storage portion to form a storage outlet;
iii) manipulating the dispensing device to cause inhalation particles travel from the storage portion into the airway of each convergent section through the feed tube while allowing the air without inhalation particles to enter into the airway in each convergent section through the bypass annulus; and
iv) dispensing inhalation particles through the air outlet of each divergent section by sequentially passing the airway through each convergent section, the throat and each divergent section.

In some embodiments, the storage portion can be fluidically coupled with the feed plate via apertures, or openings, formed by one or more storage portion puncturing elements.

Medicament inhalation particles are manufactured, or engineered, to be suitably small for example having diameters of 1 to 4 μm, such that specific areas of interest of the lung are targeted. While appropriate size ranges are often practical to achieve in manufacturing, a powder comprising inhalation particles often tends to agglomerate during handling and/or processing, including filling steps, as well as powder transferring, and storage. In such cases the powder has a tendency to agglomerate into larger than optimal particles. These powders may comprise, for example drugs plus excipients, or mixtures of drugs with carrier particles (or in some cases neat drug). Accordingly, inhalation powders are preferably deagglomerated before and/or during inhalation. A classical or conventional dry powder inhaler (DPI) normally follows these steps: medicament carried with one or more active ingredients plus carrier or excipient, stored in a container or receptacle, for example a blister (and in some cases a reservoir) is deagglomerated into particles by a DPI by either passive or active means. The need to deagglomerate can, in some cases, require a relatively high inspiratory flow for effective drug delivery to the airways. Hence one challenge in designing a passive DPI is to design structure which is effective to deagglomerate while minimizing a patient's inspiratory efforts such as inspiratory flow rate.

The magnitude of lift and drag forces depends on the difference between the air velocity and the velocity of the agglomerate particles. The venturi architecture of the throat and divergent section is effective for achieving high peak flow velocities, and hence large aerosol forces. The convergent section is able to recover a large proportion of the static pressure required to draw air through the throat. These attributes allow the high peak flow velocities to be achieved whilst limiting the airway resistance. In particular, embodiments of the present invention comprising the double venturi aerosol engine are capable of generating sufficiently large aerosol forces to result in effective deagglomeration while also minimizing patient inspiratory efforts and further delivering particulates to the mouthpiece having a sufficiently slow velocity such that inertial impaction is minimized, thus enhancing delivery to the targeted areas of the lung, producing favorable aerosolisation results. Embodiments of the present invention have been shown to yield the use results with both formulations comprising PulmoSphere™ engineered particles, as well as for other engineered particle formulations and for more conventional particle blend formulations.

A high resistance may be generated by a venturi having a narrow throat, which for a given flow rate will tend to increase air velocities and hence increase aerosol forces. However a high resistance inhaler can be uncomfortable to use, and further the generally high particle exit velocities with such high resistance inhaler designs can result in unwanted throat and tongue deposition.

Thus, it is desired to improve upon the magnitude of aerosol forces whilst significantly reducing the exit velocities of fine drug particles. It is also desirable to assure optimal aerosolization of the medicament and further to provide improved aerosol characteristics in an easily manufacturable and useable inhaler device. It is still further desirable to be able to accomplish the above in a blister-based, passive dry powder inhaler.

In one aspect of the invention, an aerosol engine for a dry powder inhaler comprises a first and a second venturi, each venturi having a convergent section and a divergent section, each convergent section having a minimum aperture, a maximum aperture, and an axial length L1, each divergent section having a minimum aperture, a maximum aperture, and an axial length L2, the convergent and divergent sections being arranged so that the minimum apertures of each abut to form a throat, each divergent and convergent section being generally conically shaped, the maximum aperture of the convergent section defining an air inlet, and the maximum aperture of the divergent section defining an air outlet, the first and second venturis being disposed such that there is a central axis intermediate to the first and second venturis; the engine further includes a first and a second powder receptacle puncturing element, operatively connected to the convergent section and parallel to but displaced from the central axis, and a third powder receptacle puncturing element arranged about the central axis, each powder receptacle puncturing element comprising a blade or piercing element; wherein each of the convergent and divergent sections and throat define an airway through which inhalation particles travel from the receptacle, and are dispensed through the air outlet.

In one version of the invention, each airway gradually decreases in volume from the air inlet towards the throat and then each airway gradually increases in volume from the throat towards the air outlet. In another version of the invention, each airway is parallel to each other along the central axis. In another version of the invention, each venturi is generally circular in cross-section.

Another aspect of the invention comprises a dispensing device for dispensing inhalation particles, the device comprising a feed plate and an aerosol engine, the aerosol engine being as described above, the feed plate comprising a feed tube, and a cone element to create, in conjunction with the inlet 112 of the aerosol engine 50, a bypass annulus. The aerosol engine is coupled to the feed plate such that inhalation particles can only pass through the feed tube from a storage portion containing inhalation particles into the airway in each convergent section and air without inhalation particles can only pass through the bypass annulus into the airway in each convergent section. In one version of the invention, the storage portion further comprises a storage outlet through which inhalation particles can exit the storage portion into the feed tube. In another version of the invention, a third powder receptacle puncturing element protrudes into the feed tube while the blade or piercing element of the third powder receptacle puncturing element stops above the storage portion such that the third powder receptacle puncturing element can be manipulated to pierce the storage portion to form the storage outlet.

Another aspect of the invention comprises a method of dispensing inhalation particles with a dispensing device, the dispensing device comprising a feed plate and an aerosol engine, the aerosol engine being as described above, the feed plate comprising the feed tube and cone element comprising the bypass annulus, the aerosol engine coupled to the feed plate such that inhalation particles can only pass through the feed tube from a storage portion for containing inhalation particles into the airway in each convergent section, and air without inhalation particles can only pass through the bypass annulus into the airway in each convergent section, the method comprising the steps of: i) coupling the storage portion onto the feed plate; ii) manipulating the storage portion to cause inhalation particles from the storage portion to enter into the airway in each convergent section through the feed tube while allowing the air without inhalation particles to enter into the airway in each convergent section through the bypass annulus; and iii) dispensing inhalation particles through the air outlet of each divergent section by sequentially passing the airway in each convergent section, throat and each divergent section.

Blister Track

Figure 3:
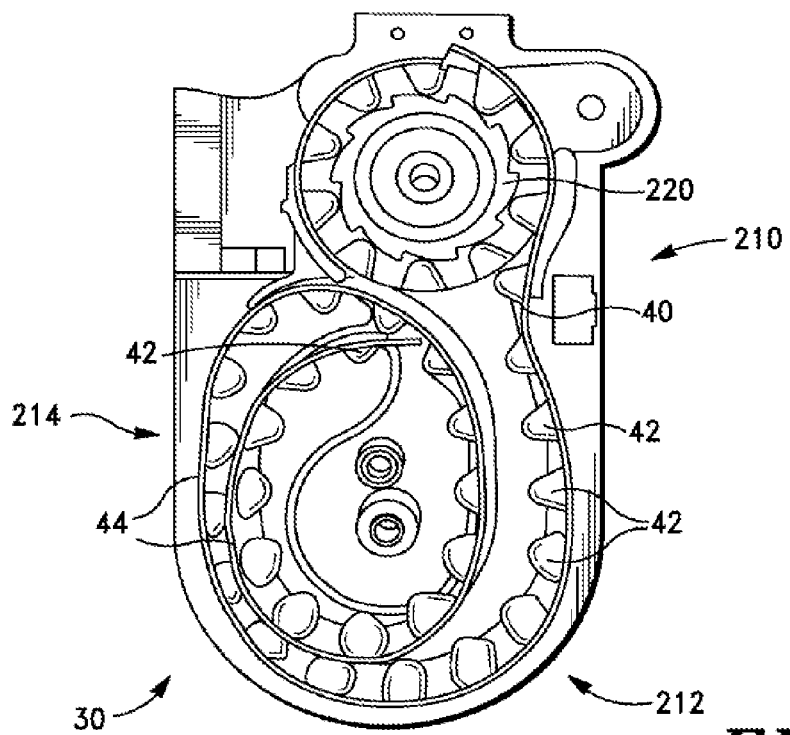
FIG. 3 is a schematic plan view of a portion of a replaceable cartridge of the present invention showing a blister track configuration according to an embodiment of the present invention.

In one embodiment, the invention comprises an inhaler device comprising the cartridge 30, and referring again to FIG. 3, there is provided a blister evacuation assembly 206, which contains structural elements which function to withdraw, or evacuate, inhalation powder from the blisters 42. In some embodiments, the blister evacuation assembly 206 comprises the pierce and retreat mechanism 60 disposed within the cartridge 30. This blister evacuation assembly 206 is adapted for facilitating withdrawal of medicament from a target blister 42 of the blister strip 40 and conveying the medicament toward an exterior of the inhaler device 10.

Blister track 44 is disposed within housing comprising the cartridge 30, and the blister track 44 is adapted for guiding each blister of the blister strip 40 to the blister evacuation assembly 206 in succession and for storing the blister strip 40 prior to, during, and after use of blisters of the blister strip. There is further provided an advancing mechanism 220, having as one element thereof index wheel 46, the advancing mechanism being adapted for advancing the blister strip 40 by a predetermined distance each time the advancing mechanism is engaged to advance the blister strip 40, the advancing mechanism 220 being actuated by user of the device 10.

In some embodiments, the advancing mechanism 220 is automatic in that it is powered by energy stored when the user manually opens a cap 300 (shown in FIG. 9) normally covering the mouthpiece 70. Similarly, in embodiments of the invention, the blister evacuation assembly 206 is automatic in that it is powered by energy stored when the user manually opens cap 300. The systems serve to provide the "open-inhale-close" functionality of the inhaler 10. By the phrase "open-inhale-close" it is meant that these are all the actions which are required of the user to obtain the desired dose and to ready the device for the next use. Thus opening the cap 300 supplies all of the energy for the various systems and subsystems, and the user's inhalation provides the threshold, or trigger, to actuate the systems necessary for dosing and advancing the blister strip. Closing the cap 300 restores the device to the ready state so it is available for the next use.

The blister evacuation assembly 206 includes components, elements or means for opening the blister 42, and aerosolizing and conveying the contents thereof to the mouthpiece 70, which in embodiments of the present invention comprises the blister piercing elements 52, and their associated translating mechanisms, while a target blister (that is the blister from which inhalation powder is to be withdrawn) is positioned in the blister evacuation assembly 206.

In some embodiments, the blister track 44 comprises a primary coil structure 210 having a first radius, a secondary coil structure 212 having a second radius, a third radius, and a fifth radius, and a tertiary coil structure 214 having the second radius, a fourth radius, and the fifth radius.

In some embodiments of the present invention, an inhaler device comprises a housing; a blister evacuation assembly disposed at least partially within the housing, the blister evacuation assembly being adapted for facilitating withdrawal of medicament from a target blister of a blister strip and conveying the medicament toward an exterior of the inhaler device, wherein the blister evacuation assembly comprises an opening element adapted for opening the target blister of the blister strip while the target blister is positioned in the blister evacuation assembly; and a dispensing element adapted for directing the withdrawn medicament toward the exterior of the inhaler device, a blister track disposed within the housing, the blister track being adapted for guiding each blister of the blister strip to the blister evacuation assembly in succession and storing the blister strip prior to, during, and after use of blisters of the blister strip, wherein the blister track comprises a primary coil structure comprising a first radius, a secondary coil structure comprising a second radius, a third radius, and a fifth radius, and a tertiary coil structure comprising the second radius, a fourth radius, and the fifth radius; an advancing mechanism disposed within the housing, the advancing mechanism being adapted for advancing the blister strip by a predetermined distance each time the advancing mechanism is engaged; and an engaging element adapted for engaging the advancing mechanism to advance the blister strip, the engaging element being operable by the user.

In embodiments of the present invention, the blister evacuation assembly, opening element, and advancing mechanism are all actuated by the user, and rely upon energy stored in the device upon an initial user actuation, for example by the user opening the cap 300 or a covering portion on the device 10. However, it is within the scope of the present invention to alternatively or additionally supply the device 10 with other forms of stored energy, the release of which can be user actuated. Such other forms of stored energy may comprise a self-contained energy supplying device within the device 10, such as a battery, or energy collection means such as photoelectric cells etc.

In some embodiments of the present invention, an inhaler device comprises a housing; a blister evacuation assembly disposed at least partially within the housing, the blister evacuation assembly being adapted for facilitating withdrawal of a medicament from a target blister of a blister strip and conveying the medicament toward an exterior of the inhaler device; and a blister advancing mechanism disposed within the housing and adapted for advancing the blister strip from an initial position where a leading edge of the blister strip is positioned in a primary coil, to a final position where the leading edge of the blister strip is positioned in a secondary coil, wherein at least the leading edge of the blister strip passes through the starting position of a trailing edge of the blister strip along the primary coil when the blister strip is advanced from the initial position to the final position.

In some embodiments of the present invention, an inhaler device comprises a blister track path and blister advance mechanism configured for providing a substantially consistent resistance to movement of the blister strip 40 therethrough.

In some embodiments of the present invention, an inhaler device comprises a blister track path and blister advance mechanism configured to provide to a user an approximately equal amount of resistance to operation of the engaging element regardless of which blister of the blister strip is positioned as the target blister.

In some embodiments of the present invention, an inhaler device comprises, a blister track path and blister advance mechanism wherein an amount of resistance to operation of the engaging element for advancing the blister strip past a first blister is about equal to an amount of resistance to operation of the engaging element for advancing the blister strip past a final blister.

The structure, arrangement, and configuration of the blister track system is more fully described in co-pending US Patent Application Publication US2015-0090262, filed 25 Sep. 2014, and assigned to the same assignee of the present invention.

Breath Actuation Mechanism

Embodiments of the inhaler device comprise automatic blister opening mechanism 75 for automatically opening the blister when the patient inhales. In one embodiment, the automatic blister opening mechanism comprises a means of using input energy from the patient (such as by opening a cap of the inhaler) to energize and latch a spring-loaded mechanism. The latch is released when the mechanism detects the patient's inhalation. When unlatched, the energy from the spring is used to pierce a blister, and also to arm a separate mechanism to index the blister strip to the next dose as the cap is closed. This automatic blister opening mechanism 75 is coupled with a breath actuated trigger mechanism 268 as described herein.

Figure 9:
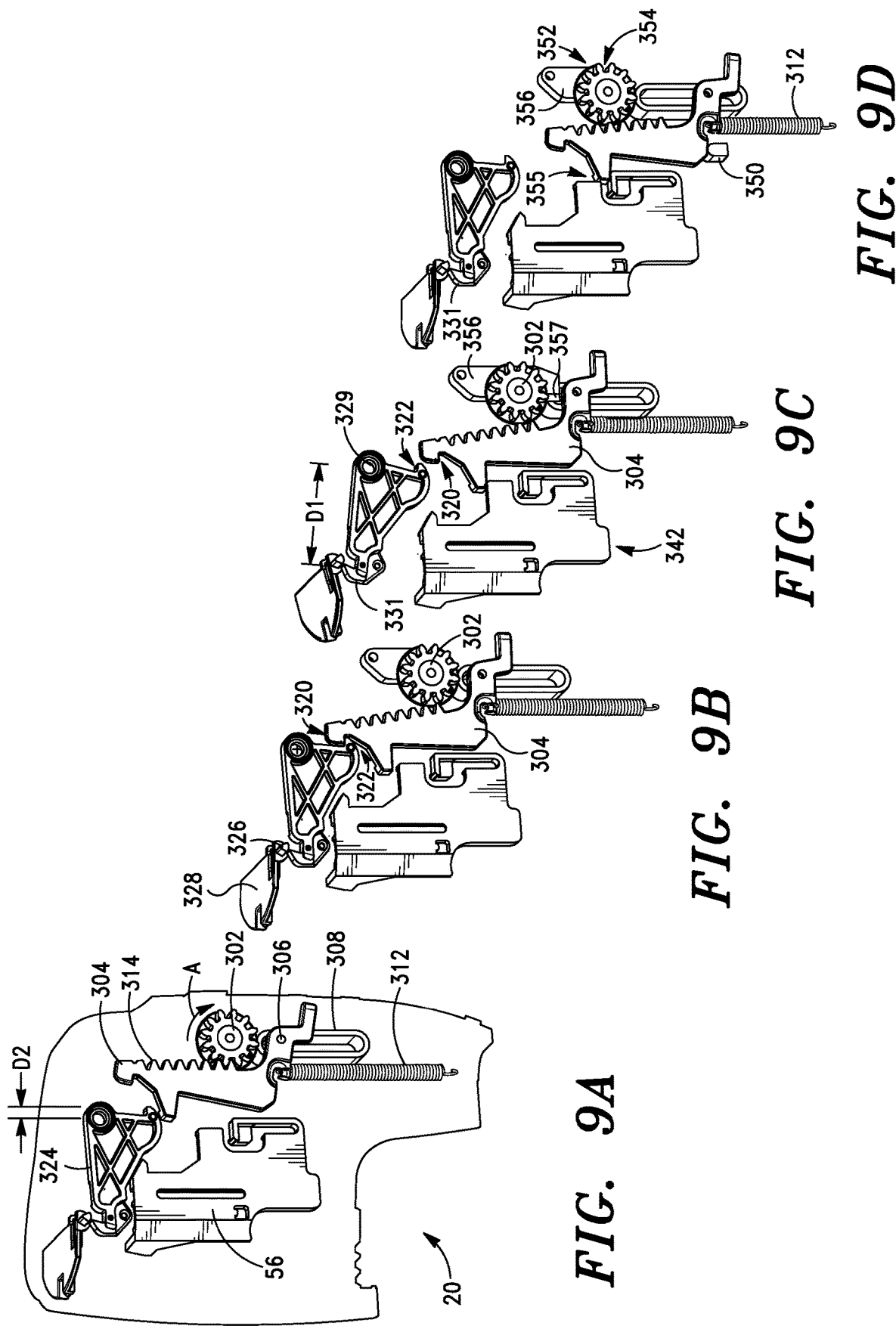
Figure 10:
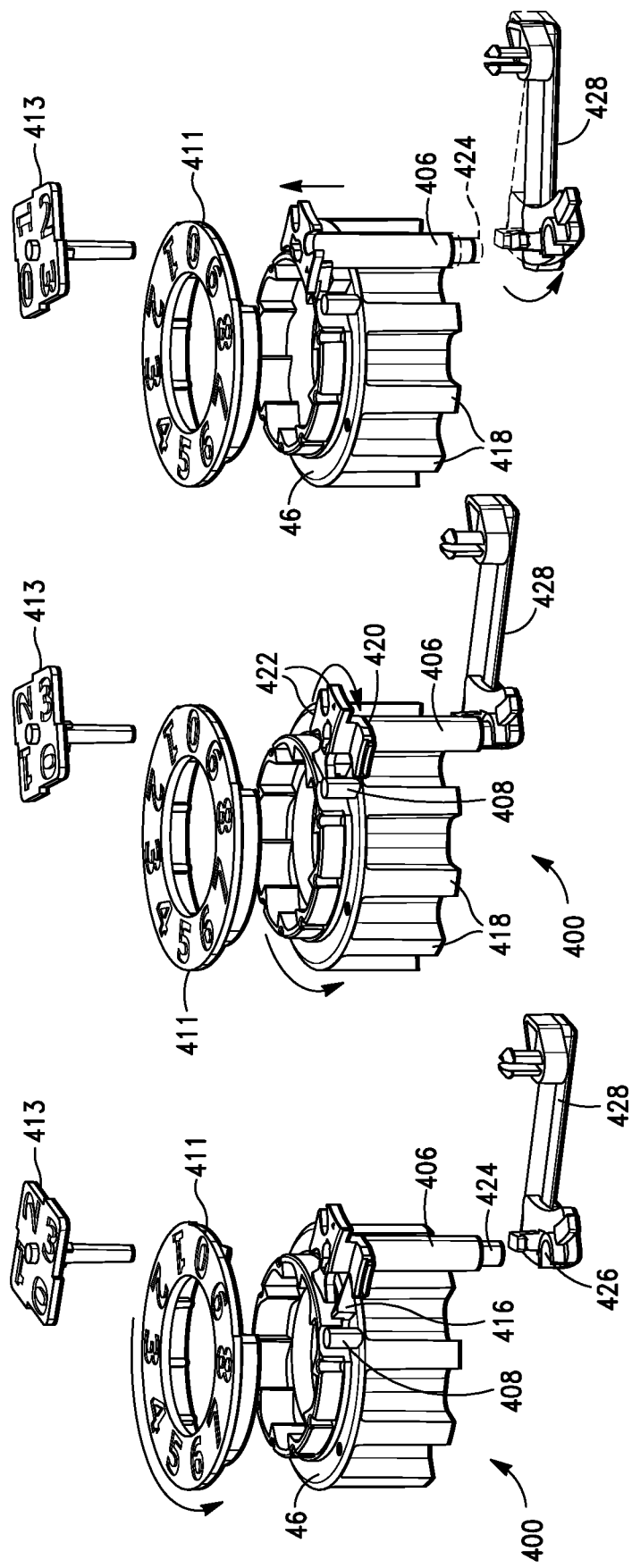

In embodiments of the invention, the breath actuated trigger mechanism comprises the following major components:
breath detection flap, spring biased clockwise
link arm, spring biased counter-clockwise
actuator arm, spring biased upwards
priming gear train support arm, spring biased clockwise
priming gear train
pivoting rack, attached to main spring
main spring
enclosure or housing; and
airbox In embodiments of the invention, the system's components are structurally and functionally as follows. Referring to FIGS. 8-10, a patient/user of the inhaler device 10 initially opens cap 300 covering the mouthpiece 70. A priming gear train 301 is mechanically engaged with and rotates with the cap 300. As the cap is opened, the primary gear train 301 imports a rotary motion to a priming gear 302, which drives a pivoting rack 304 upwards, that is in a direction which is towards the user. A pivot axle 306 on the pivoting rack 304 rides vertically in a guide 308 which is appropriately disposed within the inhaler body 20. A main spring 312 is thereby extended, which applies a counter or downward force to the pivoting rack 304, and which also results in a torque that acts to attempt to rotate the pivoting rack counter-clockwise (in the direction of arrow A as shown in FIG. 11). This torque is resisted by a single thicker or raised (compared to the smallest dimension of rack 304) tooth 314 on the pivoting rack 304 that rides against guide ribs 309a and 309b disposed within the cartridge 20 (see FIG. 8.

FIGS. 9A-9D show the full extent of the vertical travel of the pivoting rack 304 when the tooth 314 clears the top of guide rib 309a. At this point, the pivoting rack is free to rotate counter-clockwise (towards the actuator arm 56) around axle 306, which disengages the pivoting rack from the priming gear 302. Once disengaged, the cap 300 and priming gear 302 do not have any further effect on the mechanism until after the energy has been released (effectuating blister piercing, and powder aerosolization) and the cap has been closed.

Once tooth 314 on the pivoting rack clears the guide rib 309*a*, the pivoting rack rotates counter-clockwise (see FIG. 9B) and a hook 320 is captured by a ledge 322 on a link arm 324. The resulting torque on the link arm 324 is resisted by an edge of the link arm 324 abutting an axle 326 (see FIG. 9C) of a breath detection flap 328 forming a stop 327. The link arm 324 is designed and configured to have a geometry such that the large downward force from the main spring 312 is almost in line with the hook 320 and ledge 322, and thus constitutes a small moment arm (D2) with respect to a pivot axle 329 for the link arm 324, resulting in a relatively small torque. A length (D1) from the axle to an edge of the link arm creates a longer moment arm, which minimizes the contact force at the breath detection flap axle 326. In addition, there may be a spring (not shown) that biases the link arm counter-clockwise, which further reduces the contact force at the breath detection flap axle 326. The lower contact force at that interface, the less energy it takes to rotate the breath detection flap in response to the patient's inhalation efforts. In some embodiments, the force required to rotate the breath detection flap is tuned by the D1/D2 ratio.

Referring specifically to FIGS. 8 and, 9, as the patient inhales, bypass, or auxiliary, air flows through bypass air inlet apertures disposed near the top of the cartridge 30, and into an airbox 330. The airbox 330 is a plenum that is coupled to the mouthpiece 70 about one side thereof, and on the other holds the breath detection flap 328 such that all the air entering the mouthpiece 70 must go past the flap 328 and through the airbox 330. The flap 328 normally seals the airbox 330 when closed, preventing airflow therethrough. Patient inhalation causes the flap 328 to rotate downwardly which, after about 30 degrees of flap rotation (or travel) the flap encounters a bypass within the airbox which results in an unsealed configuration and allows airflow from the bypass air inlets, through the airbox and out the mouthpiece 70.

Referring again to FIGS. 9A-9D, the energy imparted by the inhalation airflow rotates the breath detection flap 328 in a counter-clockwise direction viewed from FIG. 9, which allows a tip 330 of the link arm 324 to clear the stop 327 on the axle of the breath detection flap 328. The link arm 324 is no longer able to resist the force applied to the pivoting rack 304 by the main spring 312, and the link arm rotates clockwise and releases the pivoting rack. Once released, hook 320 on the pivoting rack catches a ledge 332 on actuator arm 56 and pulls the actuator arm downwards. The downward motion of the actuator arm 56 drives the blister piercing mechanism 60 (shown in FIGS. 2 and 4), and arms an indexing mechanism, as seen in FIGS. 3, and 9-10. The indexing mechanism consists of a ratchet wheel that engages notches on index wheel 46 and serves to correctly increment blister advance. This indexing mechanism is more fully described in the above-referenced US Patent Application Publication US2015-0090262. An interlock tab 342 is used to prevent the cartridge 30 from being removed from the body 20 before the mechanism has been reset and the blister advanced to the next dose.

After a dose has been delivered, but with the cap 300 still open, the downward motion of the pivoting rack 304 is stopped by a post 350 on the body 20. At this point energy remains in main spring 310, and this energy now imparts a clockwise (viewed from the perspective of FIG. 9) torque on the pivoting rack 304, using post 350 as a fulcrum. This torque acts to urge the pivoting rack back into engagement with the priming gear, but is prevented by the thicker/raised tooth 314 on the pivoting rack bearing against a flange 352 on the priming gear 302. The flange is interrupted only at location 354, which corresponds to the position of the gear when the cap is fully closed. Thus the pivoting rack cannot reengage the priming gear train until the cap is fully closed.

The actuator arm 56 has a ledge 355 that holds the actuator arm down until the pivoting rack 304 reengages the priming gear train 301. This ensures that priming gear 302 reengages the pivoting rack 304 at the correct position.

Once the cap is fully closed, the mechanism returns to the state shown in FIG. 9D. Thus, residual energy in the main spring is use to reset the mechanisms (including the flag in the mechanical embodiments which is used to signify correct dosing), and the device is ready for the next dose.

An additional feature of the breath-actuated trigger mechanism 268 detects whether a cartridge is or is not present and disables the automatic blister opening mechanism 75 if the cartridge is not present. Priming gear train support arm 356 has a hook 357 that engages a lockout latch 428 (shown on FIG. 10) on the cartridge 30 to hold the primary gear train support arm in place during operation. If the cartridge 30 is not present, the arm is free to rotate counter-clockwise, which keeps the priming gear 302 from engaging the pivoting rack 304. This feature is also used to disable the mechanism if there are no doses left in the cartridge. Once a fresh cartridge is installed, a bias spring (not shown) on the priming gear train support arm 356 is used to reengage the hook with a complementary hook on the cartridge 30 thereby holding the priming gear train 301 in place and permitting its engagement with the pivoting rack 304.

As a result of the design and construction of this subassembly, the overall mechanism allows for a simple and relatively foolproof usage scenario and affords the "open-inhale-close" user experience.

The pivoting rack element 304 is an efficient way to couple, uncouple, and reset a driving element (cap and priming gear train) from a spring driven mechanism. This allows the energy storage to be combined with another user step (i.e. cap opening) to simplify usage.

The priming gear train support arm 356 has features that temporarily and reversibly disable the automatic opening mechanism 75 if there are no doses left in the cartridge 30, or if there is no cartridge present. This helps minimize user errors as described herein.

The link arm 324 may have an associated bias spring (not shown) which exerts a downward force (as viewed from the perspective of FIGS. 9), and supplies an additional mechanical advantage to the latch subsystem so that the energy to unlatch at the breath detection flap is as small as possible, even though the force being latched is greater than the unlatching force. This results in a much lower breath threshold to operate the device than prior art breath-actuated devices. In embodiments of the present invention, a pressure drop sufficient to trigger the breath actuated mechanism 268, resulting in actuation of the automatic opening mechanism 75, is less than about 2 kPa, or less than about 1.5 kPa or less than about 1 kPa.

Both the automatic opening blister mechanism 75 and breath actuated trigger mechanism 268 are compatible with electronic monitoring of device operation, allowing additional feedback to the user through indicator lights. The ability to provide additional feedback can help minimize user errors.

Dose Counter

In embodiments of the inhaler of the present invention, and referring to FIGS. 10, a dose counter 400 is provided and resides on the cartridge 30 wherein dose counting numerals are visible through an opening 402 in the durable unit 20. When the cartridge 30 is empty, the dose counter 400 must communicate that fact to the durable unit. This allows the device 10 to disable the automatic blister opening mechanism 75 until a new cartridge is inserted. In embodiments of the invention, the disabling acts on the primary gear train 301, to prevent it from energizing the pivoting rack 304. In embodiments of the invention, the dose counting mechanism 400 is a modified Geneva drive.

In a traditional Geneva drive a full rotation of a drive or index wheel 46 induces a sudden fractional rotation of a driven wheel 406. As shown in the Figure, a pin 408 on the drive wheel engages a slot 410 in a driven wheel 411, causing the driven wheel to rotate 90 degrees, then dwell until the pin 408 circles around again and engages the next slot 410. The amount of rotation and dwell can be tuned by adjusting the geometry.

The dose counter 400 of the present invention, in one embodiment comprises a Geneva drive mechanism comprising a drive wheel (sometimes referred to as an index wheel) 46 which is in mechanical communication with the blister strip 40. A full rotation of the drive wheel advances the blister strip by ten doses. The dose counter is a two-digit display. In embodiments of the invention, the numbers for the ones-digit are on the driven wheel comprising primary counter 411 linked directly to the drive wheel 46. After the tenth dose, a pin 408 on the drive wheel 46 turns a secondary wheel (the Geneva wheel) 406 by 90 degrees. The numbers for the tens-digit are on a secondary counter wheel 413 in mechanical communication with the secondary wheel 406.

To achieve a lockout when the cartridge 30 reaches the end of the blister strip 40, the Geneva drive mechanism is supplied with a unique condition when the counter reads "00". This unique condition comprises an auxiliary ramp 416 on the drive wheel that engages a lobe of the secondary wheel 406 which corresponds to the tens-digit "0" on the secondary counter wheel 413.

In embodiments of the present invention, the major components thus comprise:
  tens counter (linked rotationally to Geneva wheel but free to telescope along its rotational axis)
    ones-counter (linked rotationally to index wheel)
    Geneva wheel (driven wheel)
    lockout latch; and
    index wheel (drive wheel)

Referring again to FIG. 10, there is shown an exploded view of one embodiment of the dose counter mechanism 400 of the present invention. The index wheel 46 has ten ribs 418 to engage the blister tubs 42 of the blister strip. A drive pin 412 and auxiliary ramp 416 engage the Geneva wheel which has a first lobe 420 at a different height than three other lobes 422. Thus the first lobe 420 is lower than the other three lobes 422. When the Geneva wheel 406 rotates to place the first lobe 420 towards a center of the index wheel, the ramp 416 will eventually contact the first lobe 420 and push the Geneva wheel 406 outwards. A shaft end 424 of the Geneva wheel 406 is normally engaged with an arcuate surface 426 on a lockout latch 428 preventing the lockout latch 428 from rotating on its axle. The lockout latch 428 is normally biased to engage post 424. Once the Geneva wheel is pushed outwards by the ramp 416, the lockout latch 428 is then free to rotate, (as shown by the arrow in FIG. 10C) which disables the priming gear train 301, thereby preventing loading energy into main spring 312.

FIG. 10B shows the dose counter 400 just before a change from dose number 10 to 09. In this Figure, it can be seen that pin 412 is about to engage the Geneva wheel 406 as the index wheel 46 rotates from dose number 10 to dose number 09. The first, lower, lobe 420 of the Geneva wheel is now position towards the center of index wheel 46, so that the shaft end 424 of the Geneva wheel remains in contact with the arcuate surface 426 of the lockout latch 428. The mechanism remains in the state for the next $9/10$ of the revolution of the index wheel 46.

FIG. 10C shows the dose counter 400 just after a change from dose number 01 to 00. In this Figure, the ramp 416 is illustrated just after it has pushed under lower lobe 420 of the Geneva wheel. The shaft end 424 is consequently disengaged with the arcuate surface 426 of the lockout latch, so the lockout latch 428 is no longer constrained against rotation about its axis. As a result, the lockout latch may rotate which disables the priming gear train 301, which means the priming gear cannot engage with the pivoting rack and energy loading is prevented.

A hook on the lockout latch 428 is used to keep the priming gear train 301 engaged on the body 20 of the Inhaler device 10. If the lockout latch 428 is free to rotate, the priming gear train 301 cannot engage and the mechanism is disabled until a new cartridge is inserted. As discussed, when the priming mechanism is disabled, this also disables the energy storage mechanisms and prevents further blister piercing.

Embodiments of the invention described herein cover a number of interconnected elements of the device architecture. In embodiments of the invention, the, structure configuration and architecture of various systems, subsystems and elements afford a simple and relatively foolproof user experience. This in turn, mitigates a potentially significant source of dosing errors, for example failure to actually inhale a medicament, failure to administer doses regularly and others.

It is an advantage in that in embodiments of the present invention, the dose counter mechanism 400 is on replaceable cartridge 30, but is able to communicate status to the durable unit or body 20. This can result in the beneficial ability of the dose counter 400 to disable the entire device when the cartridge 30 is empty. Beneficially, in embodiments of the invention, in the absence of a cartridge 30 the dose counter mechanism 400 does not allow the device to be primed. This prevents errors in which a user may think he or she is receiving a dose but where in fact none is available.

Electronics

In some embodiments, the inhaler device optionally uses electronic circuitry to sense the status of the automatic blister opening mechanism 75 and detect the patient's breath through the mouthpiece 70. In embodiments of the invention, this circuitry functions only to monitor operation of the device 10, and does not control any aspect of the drug delivery. However, in embodiments of the invention, the electronic circuitry may be implemented in such a way as to control or assist in controlling certain aspects of the device and/or drug delivery. Moreover, the device 10 is designed with mechanical redundancy to the electrical system so that such that there is audible and/or tactile user feedback, for example a click to indicate that the dose has been received. In embodiments of the invention, the click is supplied by the sound of the latch releasing spring energy and driving the piercing mechanism.

Referring to the exemplary circuit diagram of FIG. 11, there is provided an interface between the electronics and the breath actuated trigger mechanism comprising a pressure, flow, or other applicable sensor to detect inhalation, a first and a second switch to detect when the cap is fully closed and when it is sufficiently open, and a third switch to detect when spring energy is stored in the mechanism for use by the breath-actuated dose access mechanism. The circuitry and software are used to implement the logic that turns on one of three LEDs in response to these electromechanical inputs. For example, if the cap is sufficiently open and the spring energy is properly stored in the mechanism, then the device is considered to be ready to use, and a blue LED is illuminated. If the pressure sensor indicates that a breath has occurred and the spring energy was released, then the device knows that a dose was delivered and a green LED is illuminated. The main circuit board has a switch to detect when the cap is opened, and another to detect when the spring energy is latched. The cap open switch turns on the electronics. Once the electronics are on, if the switch detects that the spring energy is latched, then the device is ready for the patient to inhale. A blue LED is illuminated to communicate that the device is ready.

In embodiments of the invention the patient inhales, and the inspiratory effort is used to actuate the breath-actuated trigger mechanism, releasing the stored spring energy to drive a lever that causes the blister to be pierced. This lever is also used to arm the blister indexing mechanism.

When the spring energy is released, in embodiments of the invention, the electronics will detect a change in the state of the latch switch. A pressure sensor can detect if the patient was inhaling at the time when the latch was released. If so, the device was operated correctly and a green LED is illuminated to communicate that the dose has been delivered. At this point, the device may use a short-range wireless protocol such as Bluetooth to send data about the dose to a hub.

Subsequent to arming of the indexing mechanism, closing the cap will drive an indexing gear train to drive the blister to the next dose. The indexing gear train communicates movement of the cap 300 to the dose counter. The dose counter will decrement (i.e. decrease from 31 to 0) as the blister is advanced. When the cap is fully closed, the residual energy in the spring is used to reset the mechanisms to their initial state and the device is then ready for the next dose.

In embodiments of the invention, a switch, such as a miniature snap action switch, or microswitch, is mounted on the blank and is in mechanical communication with the cap 300. The switch detects when the cap is fully closed. Once closed, the electronics turn off and all LEDs are turned off. The electronics remain in sleep mode until the cap is opened again.

In embodiments of the invention, an amber LED that illuminates if the software determines that there has been an error in usage. This could be due to a use error (e.g. did not inhale hard enough to trigger the BAM), a mechanical error (e.g. the device is dropped and the BAM fires), etc.

In both of the all-mechanical and the mechanical plus electronic embodiments of the device, elements are provided which detect the state of the device as having either no cartridge or an empty cartridge. Where the device detects the absence of a cartridge or an empty cartridge, the mechanical features of the device as explained hereinabove prevents the device from being primed and. In embodiments where monitoring electronics are provided, an LED is illuminated to provide additional user feedback of this state.

In some versions, the user response to an error state warning is the user is directed to check that there are doses remaining, then close the cap fully and open it again. If the error persists, the device may need replacement.

Embodiments of the invention provide connectivity between device and remote computing device (hub, server, smartphone, tablet etc.). Connectivity may be achieved as is known to the art via wireless standard and protocols, such as Bluetooth. BLE, etc, or may be via an inductive coupling to a base station, or by wired connections. In embodiments of the invention, usage is tracked and downloaded. In embodiments of the invention, user feedback may be provided additionally or alternatively through a download and subsequent upload, or independently via an alternative device such as a smartphone.

Just as the cartridge could be driven by a variety of different inhaler bodies, there are a variety of circuit board designs that could take the inputs from the available sensors, such as the pressure sensor, and/or switches to illuminate the LEDs at the appropriate time. Since the availability of specific electronic components may change, this modularity allows for the substitution of those components with suitable alternatives without affecting the aerosol delivery of the device, or the patient's user experience.

In embodiments of the invention, the electronics monitor the states of the device, such as device readiness, dose is available, etc. but are not required for the delivery of the dose. In embodiments of the invention, in addition to or as an alternative to the electronics, or if an event causes a disabling or failure of an important electronic component, a mechanical component may be available to provide user feedback, such as that of correct dosing. Such mechanical components can comprise a visual indicator such as a flag, an audible indicator such as a click or readily distinguishable sound etc.

FIG. 12 represents an exemplary software state diagram consistent with embodiments of the present invention that shows how the software will respond to various inputs from the sensors and switches. The Figure illustrates various status protocols and consequent visual indicators.

FIG. 13 is a device state diagram showing a status of various components of the device 10 over time as certain user initiated and device initiated acts and actions occur, including: device inactive, cap opened 120°, patient inhalation, cap close initiated and cap fully closed.

Inhaler Usage/Human Factors Engineering

In embodiments of the present invention, a number of human factors features are incorporated into the inhaler 10. Hence it is important that the inhaler 10 comprise simplified usability features and instructions for use. Human factors studies were conducted among two relevant user communities—chronic obstructive pulmonary disease (COPD) and asthma patients and their treating health care practitioners, and findings incorporated into the design of the inhaler of the present invention to result in a device that is intuitive, provides audio and visual feedback to the patient on correct use, and that is forgiving with regard to differences in normal patient behavior.

Functional advantages of this design process include that of the three step use method: Open-Inhale-Close, which takes into account typical human behavior and eliminates the potential for wasting doses. By minimizing the steps to administer a dose, the likelihood or errors in use is reduced by excluding any steps to prepare and insert a capsule or load a dose (e.g., push a button, twist the device). The inhaler of the present invention has been found to minimize dose preparation errors. In embodiments of the invention, dose preparation errors are less than 3% or less than 2% or less than 1%.

A key design aspect for a drug/device combination product is to build usability into the design of the device, thereby minimizing the potential for patients to commit errors. Challenges with device adherence may be associated with errors in preparing the dose to be inhaled (i.e., dose preparation errors), and in the inhalation event itself (i.e., dose inhalation errors). An intrinsic part of this human-factor design is a set of unique usability features. Thus, the inhaler of the present invention provides the simplest and most convenient dosing regimen with the fewest possible steps (i.e., 'open-inhale-close'). The breath-actuated blister access mechanism (BAM) pierces the blister on inhalation at a predetermined pressure drop, such as when about 1.5 kPa is exceeded. This eliminates the potential for wasted doses that occur in inhalers where blister piercing coincides with opening of the cap. The BAM also minimizes the impact of errors that may occur in the time between dose preparation and dose inhalation (e.g., patient exhales into the device). In general, features, systems, aspects and embodiments of the inhaler of the present invention contribute to improved patient adherence, which can itself leads to improved outcomes, that is more effective therapy with respect to a given disease or condition.

Referring again to FIGS. 11 and 12, additionally, sensory feedback to the patient on correct use of the device: light-emitting diodes (LEDs) provide feedback including ready to use (blue), dose complete (green), and error condition (amber). Audible feedback indicates that the Inhaler is operating correctly as there is a discernable click triggered by the breath actuated trigger mechanism. Embodiments of the present invention provide clear feedback when no doses are available. For example, when the dose counter reads '00', an amber LED illuminates, and the cap is easier to open due to less resistance when no doses remain in cartridge. Amber LED illuminates if no cartridge is present or the cartridge is not inserted into the durable body correctly.

In some embodiments of the present invention, and in particular when used with the herein described PulmoSpheres™ engineered particle formulations, the unique formulation of the drug mitigates certain errors traditionally associated with the inhalation maneuver when using DPIs.

In embodiments of the invention, the drug/device characteristics allow for an inhalation that does not require a large volume to be inhaled.

In embodiments the invention, the aerodynamic properties of the drug/device combination preclude significant exhalation of particles even without a breath hold.

In embodiments of the invention, there is no flow rate dependence of the inhaler. The breath actuated trigger mechanism is designed to trigger at about 1.5 kPa and the entire inhalation event is complete within about 0.5 L, ensuring the delivery of the drug across a wide range of patients from pediatrics with mild asthma to elderly patients with severe COPD.

The uncomplicated process of inhaling the drug facilitates simplified instructions for use that allow the patient to clearly understand the unique design and usability features of the Inhaler.

Two formative evaluations were undertaken, one with asthma/COPD patients and representative users, and another with health care practitioners. Findings from the evaluations indicate that: the open-inhale-close concept is easy to understand; visual indicators such as LEDs are intuitive and users are able to follow written instructions in order to troubleshoot a condition error warning symbol; user/patient training requirements are minimal; and health care practitioners and clinicians have confirmed that features of an inhaler of the present invention are suitable for patient use and it's design facilitates ease of teaching patients how to use it.

In combination with a suitable drug formulation for inspiration the inhaler 10 mitigates errors associated with dose inhalation. Breathing studies conducted with asthma and COPD patients suggest that about 97% of patients are able to achieve a pressure drop of 1.5 kPa needed to trigger a breath actuated release mechanism, thereby the full cascade of automatic mechanical operations, as well as to achieve an inhaled volume of at least about 0.5 L for effective dose delivery. When used with a formulation comprising small porous particles (for example, a PulmoSphere™ engineered particle), such as described, for example, in U.S. Pat. Nos. 6,565,885, 7,306,787, 8,168,223; 7,442,388 and 8,709,484, the inhaler 10 provides total lung deposition that is high, about 70% or greater of the nominal dose, and independent of the patient's inspiratory flow profile above about 1.0 kPa. A forceful inhalation is not a prerequisite for effective drug delivery using the inhaler 10. The breath actuated release mechanism also eliminates the impact of slow ramp rates to peak inspiratory flow on drug delivery. The high lung delivery efficiencies resulting from the design and configuration of embodiments of the inhaler 10 reduce errors associated with oropharyngeal filtering of particles. It has been found that powder (e.g. comprising inhalation particles) empties from the inhaler 10 as a bolus within the first 0.2 L of inhaled volume. This ensures that exhalation before inhalation is not a critical step in achieving effective drug delivery. Moreover, the aerodynamic particle size distribution of the porous particles ensures that a breath hold is not critical in reducing the potential for particle exhalation. These design features simplify patient instructions for use, thereby reducing many of the potential errors associated with normal patient behavior, as well as increasing comprehension of the instructions.

While described in terms of a blister-based inhaler, is within the scope of the present invention to employ the systems, assemblies, and subsystems in conjunction with receptacles other than blisters. Embodiments of the present invention, or components thereof may be used with medicament containing capsules, for example, where capsules may be linked or belted together to form either a continuous or discontinuous loop. Systems, subsystems and assemblies may suitably be utilized in different forms of either blister-based or capsule-based inhalers.

EXPERIMENTAL

Example 1

Experimental data of aerosol performance in Table 1 below with two different lots of a PulmoSphere™ drug powder having significant differences in tapped density show that the device is not sensitive to powder density. EPM=emitted powder mass, and SD=standard deviation)

TABLE 1

| Powder Lot | Tapped Density [g/cc] | 1.5 kPa EPM (SD) | 2 kPa EPM (SD) | 4 kPa EPM (SD) |
|---|---|---|---|---|
| A | 0.057 | 75 (4) | 81 (3) | 91 (2) |
| B | 0.089 | 72 (6) | 79 (5) | 88 (5) |

FIG. 14 shows the emitted mass (where EPM=emitted powder mass) of a PulmoSphere™ engineered particle formulation at three different pressure drops, using a device according to embodiments of the present invention. The fact that these three data sets are similar shows that the device has good flow rate independence.

Example 2

The influence of flow rate on the aerosol performance of an engineered spray-dried powder delivered using an inhaler according to embodiments of the invention (internally coded as the "Aspire" inhaler) was evaluated by measuring the delivered dose (DD) and total 'lung' dose (TLD). DD was measured by the mass of powder collected on a filter after exiting the device; TLD was measured by the mass of powder that was able to bypass deposition in an anatomical throat model (Alberta Idealized Throat).

Delivered dose (DD) and total lung dose (TLD) of an engineered spray-dried powder delivered using the Aspire inhaler at different pressure drops. Data are presented in Table 2 as the mean and standard deviation (shown in parentheses) of 10 and 5 replicates for DD and TLD, respectively.

TABLE 2

| Inhaler Pressure Drop [kPa] | Inhaler Flow-Rate, Q [L/min] | DD [% of Nominal] | TLD [% of Nominal] |
|---|---|---|---|
| 1.5 | 22 | 88 (3) | 76 (3) |
| 2 | 26 | 90 (5) | 76 (2) |
| 4 | 38 | 94 (2) | 82 (1) |
| 6 | 46 | 94 (3) | 80 (3) |

A metric has been defined (Weers and Clark—The Impact of Inspiratory Flow Rate on Drug Delivery to the Lungs with Dry Powder Inhalers. *Pharm. Res.* 2016, 1-22.) for quantitating the degree of flow-rate dependence, termed the Q index. The Q index is calculated from a linear regression of a plot of TLD vs. inhaler pressure drop ($\Delta P$). It represents the percent difference in TLD between pressure drops of 1.0 kPa and 6.0 kPa, normalized by the higher of the two TLD values:

$$Qindex = \frac{TLD_{6kPa} - TLD_{1kPa}}{TTLD_{higher}} \times 100\%$$

This range of pressure drops encompasses what most patients can achieve when using dry powder inhalers. The sign of the Q index indicates whether the TLD increases with $\Delta P$ (positive), or decreases with $\Delta P$ (negative). For purposes of ranking, the absolute value of the Q index is used, $|Q\ index|$. A low flow-rate dependence has been defined as having a $|Q\ index|$ less than 15%, medium flow-rate dependence as having a $|Q\ index|$ between 15% and 40%, and high flow-rate dependence as having a $|Q\ index|$ greater than 40%.

Based on the data in Table 2, the Q index of the Aspire inhaler with engineered, porous particles is +7%. Thus, this combination of a dry powder inhaler and engineered powder exhibits a low flow-rate dependence. The Q index values of a broad variety of device/powder combinations (assessed using an Alberta Idealized Throat), as reported by Weers and Clark, are provided in Table 2. Notably, the absolute value of the Q index of the Aspire inhaler with engineered, porous particles is lower than that of any of a broad variety of dry powder inhalers with powders using different formulation approaches.

TABLE 3

Q index value of Aspire in comparison to values reported for marketed products using a range of dry powder inhalers, as reported by Weers and Clark. Entries are listed in order of increasing |Q index|. Simoon is a Novartis proprietary single dose DPI (not marketed).

| Product | Drug | Formulation type | Q index (%) | Flow rate dependence |
|---|---|---|---|---|
| Aspire | [Proprietary] | Porous particle | +7.0 | Low |
| | PulmoSphere | | | |
| Simoon | Vehicle PulmoSphere | Porous particle | +12.5 | Low |
| Indacaterol Concept1 | Indacaterol | Porous particle | −14.6 | Low |
| Advair Diskus | Fluticasone | Lactose blend | +21.7 | Medium |
| | Salmeterol | | +13.9 | Low |
| Spiriva Handihaler | Tiotropium | Lactose blend | −25.0 | Medium |
| Onbrez Breezhaler | Indacaterol | Lactose blend | −31.0 | Medium |
| Asmanex Twisthaler | Mometasone | Spheronized | +62.5 | High |
| Budesonide Flexhaler | Budesonide | Spheronized | +76.0 | High |

FIG. 15 is an idealized block schematic showing relationships and disposition of certain systems and subsystems of the inhaler. In this Figure, a first block illustrates the three simple patient operations, in sequence: open cap, inhale, close cap. A second block is exemplary of how monitoring electronics may operate. Third and fourth blocks are illustrative of functional relationships of various systems and subsystems and their relative implementation locations with respect to body 20 and cartridge 30. However, it is understood that these are illustrative and not limiting; thus in embodiments of the invention, some systems illustrated as associated with the body 20 may include elements on the cartridge 30 and some systems illustrated as associated with the cartridge 30 may include elements on the body 20. Additionally, some systems or subsystems are illustrated as modular or independent may in embodiments comprise a larger or more complex system. Some systems or subsystems illustrated as modular or independent may in embodiments comprise a unitary system, for example, structure and function may be merged into a lesser number of systems or subsystems. In embodiments of the invention, some systems or subsystems may comprise a greater number of systems or subsystems than those which are illustrated in the Figure.

Having now fully described this invention, it will be understood to those of ordinary skill in the art that the methods of the present invention can be carried out with a wide and equivalent range of conditions, formulations, and other parameters without departing from the scope of the invention or any embodiments thereof. For example, most embodiments have been described in terms of having a durable or body portion and a replaceable or cartridge portion as independent elements, it may be appreciated by one skilled in the art that one could make these in a unitary manner.

All patents and publications cited herein are hereby fully incorporated by reference in their entirety. The citation of any publication is for its disclosure prior to the filing date and should not be construed as an admission that such publication is prior art.

The invention claimed is:

1. A multiple dose powder inhalation device comprising:
a body comprising an interior cavity and a cap that may be moved from a closed position to an open position;
a cartridge that is removably insertable into the interior cavity of the body, the cartridge comprising a mouthpiece through which aerosolized powder medicament may be delivered to a user, wherein the cap covers the mouthpiece when the cap is in the closed position and exposes the mouthpiece when the cap is in the open position, and wherein the cartridge houses a strip of receptacles, each receptacle adapted to contain a dose of powder medicament;
an aerosol engine adapted to aerosolize a dose of powder medicament and deliver it to the mouthpiece;
an advancing mechanism adapted to communicate with the strip of receptacles in the cartridge to selectively advance the strip of receptacles; and
a receptacle opening mechanism adapted to communicate with a piercing mechanism in the cartridge to selectively cause the piercing mechanism to create one or more openings into a receptacle, wherein the receptacle opening mechanism uses energy stored by movement of the cap.

2. A multiple dose powder inhalation device according to claim 1 wherein the receptacle opening mechanism operates to cause the piercing mechanism to create one or more openings in a receptacle that is in a piercing position so that powder medicament in the receptacle may be aerosolized by the aerosol engine and delivered to the user through the mouthpiece.

3. A multiple dose powder inhalation device according to claim 1 wherein the body further comprises electronic circuitry which monitors a state of the advancing mechanism or the receptacle opening mechanism and illuminates feedback indicators in response to state changes.

4. A multiple dose powder inhalation device according to claim 1 wherein the aerosol engine comprises a first and a second venturi, each venturi having a convergent section and a divergent section, each convergent section having a minimum aperture, a maximum aperture, and an axial length L1, each divergent section having a minimum aperture, a maximum aperture, and an axial length L2, the convergent and divergent sections being arranged so that the minimum apertures of each abut to form a throat, each divergent and convergent section being generally conically shaped, the maximum aperture of the convergent section defining an air inlet, and the maximum aperture of the divergent section defining an air outlet, the first and second venturis being disposed such that there is a central axis intermediate to the first and second venturis; and the piercing mechanism further including a first and a second powder receptacle puncturing element, operatively connected to the convergent section and parallel to but displaced from the central axis, and a third powder puncturing element arranged about the central axis, each powder receptacle puncturing element comprising a blade or piercing element; wherein each of the convergent and divergent sections and throat define an airway through which inhalation particles travel and can be dispensed through the air outlet.

5. The multiple dose powder inhalation device of claim 1 wherein the cartridge further comprises a dose lockout mechanism and wherein the dose lockout mechanism prevents further use of the cartridge under predetermined conditions.

6. A multiple dose powder inhalation device according to claim 1 wherein the automatic receptacle opening mechanism comprises a breath-actuated mechanism adapted to cause the piercing mechanism to create the one or more openings into the receptacle in response to a breath of the user.

7. A multiple dose powder inhalation device according to claim 6 wherein the breath-actuated mechanism comprises a lever coupled to a pinion gear; a rack gear engaged with the pinion gear adapted to urge a the rack in a first direction, the rack gear including a first latch; a spring adapted to bias the rack gear in a direction opposed to the first direction; a pivotable link bar having a second latch adapted to engage with the first latch, the pivotable link bar being in mechanical communication with a breath actuation flap wherein movement of the pivotable link bar stores energy in the bias through the rack gear and pinion gear as the rack gear is urged in the first direction, whereupon the first latch and second latch engage, and upon breath actuation of the flap, the first latch and the second latch disengage, releasing the stored energy; and wherein a breath actuation energy is 2 kPa or less.

8. A multiple dose powder inhalation device according to claim 1 wherein the automatic receptacle opening mechanism comprises a breath-actuated mechanism adapted to cause the piercing mechanism to create the one or more openings into the receptacle in response to a breath of the user and while the cap is in the open position.

9. A method of delivering by pulmonary administration a medicament in powder form, the method comprising:
providing a multiple dose powder inhalation device according to claim 1; and
opening the cap, inhaling the medicament and closing the cap.

10. A multiple dose powder inhalation device comprising:
a body comprising an interior cavity and
a cartridge that is removably insertable into the interior cavity of the body, the cartridge comprising a mouthpiece through which aerosolized powder medicament may be delivered to a user,
wherein the cartridge houses a strip of receptacles, each receptacle adapted to contain a dose of powder medicament, a dose counting mechanism, a receptacle opening mechanism and an aerosol generating mechanism, and
wherein the body comprises a cap that may be moved from a closed position that covers the mouthpiece to an open position that exposes the mouthpiece, wherein the movement of the cap to the open position causes a spring to become latched in a biased position, and
wherein the receptacle opening mechanism comprises a breath-actuated mechanism that unlatches the biased spring to cause a receptacle to be pierced.

11. A multiple dose powder inhalation device comprising:
a body comprising an interior cavity, a priming mechanism, and a drive indexing mechanism, and
a cartridge that is removably insertable into the interior cavity of the body, the cartridge comprising a mouthpiece through which aerosolized powder medicament may be delivered to a user, wherein the cartridge comprises a strip of receptacles, each receptacle adapted to contain a dose of powder medicament, the cartridge further comprises a receptacle piercing mechanism and an aerosol generating mechanism, wherein the body communicates with the cartridge to cause actuation of the receptacle piercing mechanism and to cause advancement of the strip of receptacles.

12. The multiple dose powder inhalation device of claim 11 wherein the body further comprises a cap that may be moved from a closed position that covers the mouthpiece to an open position that exposes the mouthpiece and wherein the movement of the cap from the open position to the closed position causes the strip of receptacles to be advanced in the cartridge.

13. A multiple dose powder inhalation device according to claim 11 wherein the body further comprises electronic circuitry which monitors a state of the receptacle piercing mechanism or the aerosol generating mechanism and illuminates feedback indicators in response to state changes.

14. The multiple dose powder inhalation device of claim 11 wherein the body further comprises a cap that may be moved from a closed position that covers the mouthpiece to an open position that exposes the mouthpiece and wherein the movement of the cap from the open position to the closed position causes the priming mechanism to prime the device.

* * * * *